(12) United States Patent
Casper et al.

(10) Patent No.: US 7,846,957 B2
(45) Date of Patent: *Dec. 7, 2010

(54) AROMATASE INHIBITION TO ENHANCE ASSISTED REPRODUCTION

(75) Inventors: Robert F. Casper, Toronto (CA); Mohamed F. M. Mitwally, North York (CA)

(73) Assignee: Ares Trading S.A., Aubonne (CH)

( * ) Notice: Subject to any disclaimer, the term of this patent is extended or adjusted under 35 U.S.C. 154(b) by 1274 days.

This patent is subject to a terminal disclaimer.

(21) Appl. No.: 10/475,172

(22) PCT Filed: Apr. 17, 2002

(86) PCT No.: PCT/CA02/00522

§ 371 (c)(1),
(2), (4) Date: May 25, 2004

(87) PCT Pub. No.: WO02/083240

PCT Pub. Date: Oct. 24, 2002

(65) Prior Publication Data

US 2004/0204393 A1  Oct. 14, 2004

Related U.S. Application Data

(60) Provisional application No. 60/284,178, filed on Apr. 17, 2001.

(51) Int. Cl.
*A61K 31/56* (2006.01)
*A61K 31/41* (2006.01)

(52) U.S. Cl. .......................... 514/383; 514/2; 514/177; 546/210

(58) Field of Classification Search ................. 546/210; 514/2, 177, 383
See application file for complete search history.

(56) References Cited

U.S. PATENT DOCUMENTS

| 4,289,762 | A | * | 9/1981 | Metcalf et al. | 514/179 |
| 4,728,645 | A | * | 3/1988 | Browne | 514/210.16 |
| 4,845,227 | A | * | 7/1989 | Hirsch et al. | 548/250 |
| 4,978,672 | A | * | 12/1990 | Bowman et al. | 514/383 |
| 6,015,789 | A | * | 1/2000 | Suzuki et al. | 514/15 |
| 6,953,774 | B2 | * | 10/2005 | Palmer et al. | 514/2 |

FOREIGN PATENT DOCUMENTS

| DE | 43 30 237 | 3/1995 |
| DE | 196 22 457 | 11/1997 |
| EP | 907 351 B1 | 4/1999 |
| WO | WO-97/40846 | 11/1997 |
| WO | WO 9858657 A1 * | 12/1998 |

OTHER PUBLICATIONS

Hamilton et al., "The third-generation non-steroidal aromatase inhibitors: A review of their clinical benefits in the second-line hormonal treatment of advanced breast cancer." Annals of Oncology 1999:10;377-384.*

Homburg et al., "Low-dose FSH therapy for anovulatory infertility associated with polycystic ovary syndrome: rationale, results, reflections and refinements." Human Reproduction Update 1999:5(5);493-499.*

Mu et al., "Insulin Sensitizer, Troglitazine, Directly Inhibits Aromatase Activity in Human Ovarian Granulosa Cells." Biochemical and Biophysical Research Communications 2000: 710-713.*

Mitwally et al., "High ovulatory rates with use of Troglitazone in clomiphene-resistant women with polycystic ovary syndrome." Human Reproduction 1999:14(11);2700-2703.*

Dowsett, "Aromatase inhibitors come of age." Annals of Oncology 1997:8;631-632.*

Doldi et al., "Elevated serum progesterone on the day of HCG administration in IVF is associated with higher pregnancy rate in polycystic ovary syndrome." Human Reproduction 1999:14(3);601-605.*

DrugBank: DB00197 (Troglitazone) at http://www.drugbank.ca. Date: Jun. 13, 2005.*

Adashi, "Clomiphene Citrate: Mechanism(s) and site(s) of Action—a Hypothesis Revisited," *Fertil Steril*, vol. 42, No. 3, pp. 331-344 (1984).

Akhtar et al., "Mechanistic Studies on Aromatase and Related C-C Bond Cleaving P-450 Enzymes," *J. Steroid Biochem Mol Biol*, vol. 44, pp. 375-387 (1993).

Archer et al., "Effects of Clomiphene Citrate on Episodic Luteinizing Hormone Secretion Throughout the Menstrual Cycle," *Am J. Obstet Gynecol*, vol. 161, No. 3, pp. 581-589 (1989).

Basir et al., "Morphometric Analysis of Pen-Implantation Endometrium in Patients Having Excessively High Oestradiol Concentrations After Ovarian Stimulation," *Hum. Reprod.*, vol. 16, No. 3, pp. 435-440 (2001).

Bateman et al., "Exogenous Estrogen Therapy for Treatment of Clomiphene Citrate—Induced Cervical Mucus Abnormalities: Is It Effective?" *Fertil Steril*, vol. 54, pp. 577-579 (1990).

Ben-Ami et al., "Exogenous Estrogen Therapy Concurrent with Clomiphene Citrate—Lack of Effect on Serum Sex Hormone Levels and Endometrial Thickness," *Gynecol Obstet Invest*, vol. 37, No. 3, pp. 180-182 (1994).

(Continued)

*Primary Examiner*—Frederick Krass
*Assistant Examiner*—Walter E Webb
(74) *Attorney, Agent, or Firm*—Marshall, Gerstein & Borun LLP

(57) ABSTRACT

The use of at least one aromatase inhibitor in the production of a medicament for improving the implantation and pregnancy rates for a female undergoing assisted reproduction treatment, which comprises one or more daily doses of an aromatase inhibitor (AI) for administration during assisted reproduction cycles or ovarian stimulation cycles, wherein the doses of AI are selected from amounts effective to reduce serum estradiol levels. Also disclosed are related pharmaceutical preparations and packages.

25 Claims, No Drawings

OTHER PUBLICATIONS

Cole et al., "Mechanism and Inhibition of Cytochrome P-450 Aromatase," *J. Med. Chem.*, vol. 33, pp. 2933-2944 (1990).

Coombes et al., "4-Hydroxyandrostenedione Treatment of Postmenopausal Patients with Advanced Breast Cancer," *The Lancet 2*, pp. 1237-1239 (1984).

Dickey et al., "Observations on the Mechanism of Action of Clomiphene (MRL-41)," *Fertil Steril*, vol. 16, pp. 485-494 (1965).

Dowsett et al., "Vorozole Results in Greater Oestrogen Suppression Than Formestane in Postmenopausal Women and When Added to Goserella in Premenopausal Women with Advanced Breast Cancer," *Breast Cancer Research and Treatment*, vol. 56, No. 1, pp. 25-34 (1999) (Abstract).

Fisch et al., "Unexplained Infertility: Evaluation of Treatment with Clomiphene Citrate and Human Chorionic Gonadotropin," *Fertil Steril*, vol. 51, pp. 828-833 (1989).

Fluker et al., "Exogenous Gonadotropin Therapy in World Health Organization Groups I and II Ovulatory Disorders," *Obstet Gynecol*, vol. 83, pp. 189-196 (1994).

Forman et al., "Evidence for an Adverse Effect of Elevated Serum Estradiol Concentration on Embryo Implantation," *Fertil Steril*, vol. 49, pp. 118-121 (1988).

Garcia et al., "Advanced Endometrial Maturation After Ovulation Induction with Human Menopausal Gonadotropin/Human Chorionic Gonadotropin for in Vitro Fertilization," *Fertil Steril*, vol. 41, pp. 31-35 (1984).

Garcia et al., "The Use of Clomiphene Citrate," *Fertil Steril*, vol. 28, pp. 707-717 (1997).

Geisler et al., "Influence of Anastrozie (Arimidex), a Selective, Non-Steroidal Aromatase Inhibitor, on In Vitro Aromatisation and Plasma Oestrogen Levels in Postmenopausal Women with Breast Cancer," *Br J Cancer*, vol. 74, pp. 1286-1291 (1996).

Gelety et al., "The Effect of Clomiphene Citrate and Menopausal Gonadotropins on Cervical Mucus in Ovulatory Cycles," *Fertil Steril*, vol. 60, pp. 471-476 (1993).

Goldfarb et al., "Critical Review of 160 Clomiphene-related Pregnancies," *Obstet Gynecol*, vol. 31, pp. 342-345 (1968).

Gonen et al., "Determination of an Adverse Effect of Clomiphene Citrate on Endometrial Growth," *Hum Reprod*, vol. 5, pp. 670-674 (1990).

Graf et al., "Histologic Evaluation of the Luteal Phase in Women Following Follicle Aspiration for Oocyte Retrieval," *Fertil Steril*, vol. 49, pp. 616-619 (1988).

Hadi et al., "Ovulation Induction and Endometrial Steroid Receptors," *Hum. Reprod.*, vol. 9, pp. 2405-2410 (1994).

Kettel et al., "Hypothalamic-pituitary-ovarian Response to Clomiphene Citrate in Women with Polycystic Ovary Syndrome," *Fertil Steril*, vol. 59, No. 3, pp. 532-538 (1993).

Kolb et al., "Ultrastructural Characteristics of the Luteal Phase Endometrium in Patients Undergoing Controlled Ovarian Stimulation," *Fertil Steril*, vol. 67, pp. 625-630 (1997).

Macrow et al., "Endometrial Structure After Superovulation: A Prospective Controlled Study," *Fertil Steril*, vol. 61, pp. 696-699 (1994).

Mikkelson et al., "Single-dose Pharmacokinetics of Clomiphene Citrate in Normal Volunteers," *Fertil Steril*, vol. 46, pp. 392-396 (1986).

Mitwally et al., "Aromatase Inhibition for Ovarian Stimulation: Future Avenues for Infertility Management," *Current Opinion in Obstetrics & Gynecology*, vol. 14 (2002) (Abstract).

Mitwally et al., "Aromatase Inhibition Improves Ovarian Response to Follicle-Stimulating Hormone in Poor Responders," *Fertility & Sterility*, vol. 77, pp. 776-780 (2002) (Abstract).

Mitwally et al., "Use of an Aromatase Inhibitor for Induction of Ovulation in Patients with an Inadequate Response to Clomiphene Citrate," *Fertil Steril*, vol. 75, No. 2, pp. 305-309 (2001).

Nargund et al., "Cumulative Conception and Live Birth Rates in Natural (unstimulated) IVF Cycles," *Hum. Reprod.*, vol. 16, pp. 259-262 (2001).

Nebert et al., "The P-450 Superfamily: Update on New Sequences, Gene Mapping and Recommended Nomenclature," *DNA Mol. Biol.*, vol. 10, pp. 1-14 (1991).

Ng et al., "High Serum Oestradiol Concentration in Fresh IVF Cycles do not Impair Implantation and Pregnancy Rates in Subsequent Frozen-Thawed Embryo Transfer Cycles," *Hum. Reprod.*, vol. 15, pp. 250-255 (2000).

Noci et al., "Hormonal Patterns, Steroid Receptors and Morphological Pictures of Endometrium in Hyperstimulated IVF Cycles," *Eur. J. Obstet. Gynecol. Reprod. Biol.*, vol. 75, pp. 215-220 (1997).

Paulson et al., "Factors Affecting Embryo Implantation After Human In Vitro Fertilization: A Hypothesis," *Am J Obstet Gynecol*, vol. 163, pp. 2020-2023 (1990).

Randall et al., "Cervical Mucus Score and In Vitro Sperm Mucus Interaction in Spontaneous and Clomiphene Citrate Cycles," *Fertil Steril*, vol. 56, pp. 465-468 (1991).

Saleh et al., "Effects of Tamoxifen (Tx) on Endometrial Thickness and Pregnancy Rates in Women Undergoing Superovulation with Clomiphene Citrate (CC) and Intrauterine Insemination (IUI)," *Fertil Steril*, vol. 74, No. S1, pp. S90 (2000).

Santen et al., "Endocrine Treatment of Breast Cancer in Women," *Endocrine Rev*, vol. 11, pp. 1-45 (1990).

Santen et al., "Successful Medical Adrenalectomy with Aminoglutethimide: Role of Altered Drug Metabolism," *J. Am. Med. Assoc.*, vol. 230, pp. 1661 (1974).

Seif et al., "Endometrium in In-Vitro Fertilization Cycles: Morphological and Functional Differentiation in the Implantation Phase," *Hum. Reprod.*, vol. 7, pp. 6-11 (1992).

Sereepapong et al., "Effects of Clomiphene Citrate on the Endometrium of Regularly Cycling Women," *Fertil Steril*, vol. 73, pp. 287-291 (2000).

Shetty et al., "Effect of Estrogen Deprivation on the Reproductive Physiology of Male and Female Primates," *J Steroid Biochem Biol*, vol. 61, pp. 157-166 (1997).

Simon et al., "Clinical Evidence for a Detrimental Effect on Uterine Receptivity of High Serum Oestradiol Concentrations in High and Normal Responder Patients," *Hum. Reprod.*, vol. 10, pp. 2432-2437 (1995).

Simon et al., "Increasing Uterine Receptivity by Decreasing Estradiol Levels During the Preimplantation Period in High Responders with the Use of a Follicle-Stimulating Hormone Step-Down Regimen," *Fertil Steril*, vol. 70, pp. 234-239 (1998).

Sinha et al., Effects of CGS20267 on Ovarian Aromatase and Gonadotropin Levels in the Rat, *Breast Cancer Res Treat*, vol. 48, pp. 45-51 (1998).

Sioufi et al., "Absolute Bioavailability of Letrozole in Healthy Postmenopausal Women," *Biopharm Drug Dispos*, vol. 18, pp. 779-789 (1997).

Sioufi et al., "Comparative Bioavailability of Letrozole Under Fed and Fasting Conditions in 12 Healthy Subjects After a 2.5 mg Single Oral Administration," *Biopharm Drug Dispos*, vol. 18, No. 6, pp. 779-797 (1997).

Sterzik et al., "In Vitro Fertilization: The Degree of Endometrial Insufficiency Varies with the Type of Ovarian Stimulation," *Fertil Steril*, vol. 50, pp. 457-462 (1988).

Taymor, "The Regulation of Follicle Growth: Some Clinical Implications in Reproductive Endocrinology," *Fertil Steril*, vol. 65, No. 2, pp. 235-247 (1996).

Tortoriello et al., "'Coasting' Does Not Adversely Affect Cycle Outcome in a Subset of Highly Responsive In Vitro Fertilization Patients," *Fertil Steril*, vol. 69, No. 3, pp. 454-460 (1998).

Trunet et al., "Open Dose-Finding Study of a New Potent and Selective Nonsteroidal Aromatase Inhibitor, CGS 20 267, in Healthy Male Subjects," *J Clinc Endocrinol Metab*, vol. 77, pp. 319-323 (1993).

Valbuena et al., "Increasing Levels of Estradiol are Deleterious to Embryonic Implantation Because They Directly Affect the Embryo," *Fertil Steril*, Vol. 76, pp. 962-968 (2001).

Vendola et al., "Androgens Stimulate Early Stages of Follicular Growth in the Primate Ovary," *J Clin Invest*, vol. 101, No. 12, pp. 2622-2629 (1998).

Weil, et al., "Androgen and Follicle-Stimulating Hormone Interactions in Primate Ovarian Follicle Development," *J Clin Endocrinol Metab*, vol. 84, No. 8, pp. 2951-2956 (1999).

Wu et al., "The Effect of Therapy Initiation Day on Clomiphene Citrate Therapy," *Fertil Steril*, vol. 52, pp. 564-568 (1989).

Wysowski, "Use of Fertility Drugs in the United States, 1979 through 1991," *Fertil Steril*, vol. 60, pp. 1096-1098 (1993).

Yagel et al., "The Effect of Ethinyl Estradiol on Endometrial Thickness and Uterine Volume During Ovulation Induction by Clomiphene Citrate," *Fertil Steril*, vol. 57, pp. 33-36 (1992).

Mohamed F. Mitwally et al, "Aromatase Inhibiton for Ovarian Stimulation: Future Avenues for Infertility Management", Current Opinion in Obstetrics & Gynecology, England, Jun. 2002, vol. 14, No. 3, pp. 255-263.

Mohamed Farouk Mitwally et al, "Aromatase Inhibition Improves Ovarian Response to Follicle-Stimulating Hormone in Poor Responders", Fertility and Sterility. United States Apr. 2002, vol. 77, No. 4, Apr. 2002, pp. 776-780.

"The Ovulatory Cycle and Drug Therapy—Letrozole Protocol", Internet, 'Online!, Feb. 2001, Retrieved from the internet: URL:http://www.baby-makers.com/theovulatorycycleand-drugtherapy.html, retrieved on Jul. 10, 2002.

Mohamed F. M. Mitwally et al, "Use of an Aromatase Inhibitor for Induction of Ovulation in Patients With an Inadequate Response to Clomiphene Citrate", Fertility and Sterility, vol. 75, No. 2, Feb. 2001, pp. 305-309.

M. F. Mitwally et al, "The Use of an Aromatase in Cases of Clomiphen Citrate Failure", Human Reproduction (Oxford), vol. 15, No. Abstract Book 1, Jun. 2000, pp. 71-72.

MFM Mitwally et al, "The Aromatase Inhibitor Letrozole: A Promising Alternative for Clomiphene Citrate for Induction of Ovulation" Abstract No. 0-91 in: Program and Abstracts of the 56$^{th}$ Annual Meeting of the American Society for Reproductive Medicine (ASRM), Oct. 2000, San Diego (CA), USA.

MFM Mitwally et al, "Aromatase Inhibition Decreases FSH Dose Needed During Controles Ovarian Hyperstimulation: A Controlled Perspective Trial", J. Soc. Gynecol. Investig., vol. 8, No. 1 (Supplement) Feb. 2001, pp. 85A.

Mohamed F. Mitwally et al, "Aromatase Inhibition: A Novel Method of Ovulation Induction in Women With Polycyctic Ovary Syndrome", Reproductive Technologies, vol. 10, No. 5, 2000, pp. 244-247.

MFM Mitwally et al, "Aromatase Inhibition Improves Ovarian Response to FSH: A Potential Option for Low Responders During Ovarian Stimulation", Abstract No. 0-9, in Abstracts of the 48$^{th}$ Meeting of the Pacific Coast Fertility Society, Apr. 2001, Rancho Las Palmas Resort and Spa, CA, USA.

ML Feutrie et al, "Aromatase Inhibitors!", Bulletin DU Cancer,France, Oct. 1999, vol. 86, No. 10, Oct. 1999, pp. 821-827.

RC Coombes et al, "Aromatase Inhibitors and Their Use in the Sequential Setting", Endocrine-Related Cancer, Journal of Endocrinology LTD., Bristol, GB, vol. 6, No. 2, Jun. 1999, pp. 259-263.

A. Sioufi et al, "Absolute Bioavailability of Letrozole in Healthy Postmenopausal Women", Biopharmaceutics & Drug Disposition, England Dec. 1997, pp. 779-789.

M. Dowsett et al, "Anastrozole—A New Generation in Aromatasw Inhibition: Clinical Pharmacology", Oncology, Switzerland 1997, vol. 54Suool 2, 1997, pp. 11-14.

Allan Lipton et al, "Letrozole (CGS 20267): A Phase I Study of a New Potent Oral Aromatase Inhibitor of Breast Cancer", Cancer (Philadelphia), vol. 75, No. 8, 1995, pp. 2131-2138.

Mitchell Dowsett et al, "Vorozole Results in Greater Oestrogen Suppression Than Formestane in Postmenopausal Women and When Added to Goserella in Premenopausal Women With Advanced Breast Cancer" Breast Cancer Research and Treatment, Nijhoff, Boston, US, vol. 56, No. 1, Jul. 1, 1999, pp. 25-34.

Dixon et al., "Lessons From the Use of Aromatase Inhibitors in the Neoadjuvant Setting", *Endocrine-Related Cancer*, 6:227-230 (1999).

Lonning, "Cross-Resistance to Different Aromatase Inhibitors in Breast Cancer Treatment", *Endocrine-Related Cancer*, 6:251-257 (1999).

Miller, "Aromatase Inhibitors: Mechanism of Action and Role in the Treatment of Breast Cancer", *Seminars in Oncology*, 30(4) (Suppl 14):3-11 (2003).

Tahara et al., "Successful Preparation of Metabolite of Troglitazone by In-Flow Electrochemical Reaction on Coulometric Electrode", *Chem Phar. Bull.*, 55(8):1207-1212 (2007).

Afonso et al., "Effects of the Aromatase Inhibitor Fadrozole on Plasma Sex Steroid Secretion and Ovulation Rate in Female Coho Salmon, Oncorhynchus kisutch, Close to Final Maturation", General and Comparative Endocrinology, 113:221-229 (1999).

Mitwally et al., The Aromatase Inhibitor, Letrozole, Decreases FSH Dose Required for Ovarian Superovulation, CFAS meeting: Newfoundland, Canada, Sep. 2000.

Mitwally et al., Aromatase Inhibition Improves Response to Controlled Ovarian Hyperstimulation Without the Antiestrogenic Effects of Clomiphene Citrate, ESHRE meeting: Lausanne, Switzerland, Jul. 2001.

Database Pharmaprojects 'Online ' PJB Publications LTD. UK "Exemestane" Database accession No. 4447, (1985).

Database Pharmaprojects 'Online' PJB Publications LTD. UK "letrozole" Database accession No. 2585, (1986).

Coombes et al., Aromatase Inhibitors and Their Use in the Sequential Setting, Endocrine-Related Cancer, 6:259-263 (1999).

Database Pharmaprojects 'Online' PJB Publications LTD. UK "Exemestane" Database Accession No. 4447, Date: Jul. 9, 1985.

Database Pharmaprojects 'Online' PJB Publications LTD. UK "Letrozole" Database Accession No. 2585, Date: Mar. 7, 1986.

Dowsett, "Biological Background to Aromatase Inhibition," *The Breast*, vol. 5, pp. 196-201 (1996).

Feutrie, "Aromatase Inhibitors," *Bulletin du Cancer*. vol. 86, No. 10, pp. 821-827 (1990).

Marty et al., "ALS, a New Potent, Selective Aromatase Inhibitor Superior to Aminoglutethimide (AG) in Postmenopausal Women With Advanced Breast Cancer Previously Treated With Antioestrogens," *Proc Am Soc Clim Oncol*, vol. 16, pp. 156 (1997).

Mitwally et al., "Aromatase Inhibition Decreases FSH Dose Needed During Controlled Ovarian Hyperstimulation: A Controlled Prospective Trial," Meeting of the Society for Gynecologic Investigation, Abstract published in *J. Soc. Gynecol. Invest.*, vol. 8, pp. 85A (2001).

Mitwally et al., "Aromatase Inhibition Improves Ovarian Response to FSH: A Potential Option for Low Responders During Ovarian Stimulation," The 48$^{th}$ Meeting of the Pacific Coast Fertility Society Meeting, Rancho Las Palmas Resort and Spa, (2001).

Mitwally et al., "Aromatase Inhibition: A Novel Method of Ovulation Induction in Women With Polycystic Ovarian Syndrome," *Reprod Technol*, vol. 10, No. 5, pp. 244-247 (2001).

Mitwally et al., "The Aromatase Inhibitor, Letrozole: a Promising Alternative for Clomiphene Citrate for Induction of Ovulation," Program and Abstracts of the 56$^{th}$ Annual Meeting of the American Society for Reproductive Medicine (ASRM), Oct. 2000, San Diego.

Mitwally et al., "The Use of an Aromatase Inhibitor for Induction of Ovulation in Cases of CLomiphene Citrate Failure," *Hum. Reprod.*, vol. 16, pp. 71-72 (2000).

The Ovulatory Cycle and Drug Therapy-Letrozole Protocol: Internet "Online Feb. 2001"; http://www.baby-makers.com/theovulatorycycleanddrugtherapy.html.

* cited by examiner

AROMATASE INHIBITION TO ENHANCE ASSISTED REPRODUCTION

FIELD OF THE INVENTION

This invention relates to a method for treating females undergoing assisted reproduction treatment and ovulation induction which involves administration of an aromatase inhibitor (AI). Also disclosed are preparations and related uses. There is also described a method for increasing production of follicles in a female for the purpose of harvesting immature eggs for oocyte maturation in vitro which also involves the administration of AI.

BACKGROUND OF THE INVENTION

In most assisted reproduction programs, gonadotropins are used alone or in combination to stimulate the growth and maturation of multiple oocytes. This is essential because of the need to recruit a greater number of follicles, which improves the chance of fertilization and an increased number of embryos for transfer to give acceptable success rates. Recent advances in the understanding of ovarian stimulation, the techniques of oocyte retrieval, the handling of gametes, the methods of assisted fertilization and improved conditions of culture media have steadily increased the fertilization rate. Oocyte fertilization rates of 60-70% can now be expected when conventional insemination or intracytoplasmic sperm injection (ICSI) are carried out. However, there has not been a corresponding increase in implantation rates, which have remained steady at 10-15% per embryo[1].

It is believed that the high, supraphysiologic levels of estrogen, attained during ovarian stimulation, may result in an adverse effect of ovarian stimulation on the outcome of infertility treatment. Significant decreases in pregnancy and implantation rates have been observed when estradiol concentrations were >10,000 pmol/L compared with patients having lower estradiol concentrations[2]. High serum estradiol concentrations on the day of HCG injection in IVF patients, regardless of the number of oocytes retrieved, were found to be detrimental to uterine receptivity[3]. Recently, it has been shown that a significant reduction in implantation and pregnancy rates occurred in almost all women with a serum estradiol concentration greater than 20,000 pmol/L[4].

Different mechanisms have been postulated to explain the adverse effect of the supraphysiologic levels of estrogen including deleterious effects on the endometrium and the embryo, although the exact mechanisms have not yet been determined.

Effect of Supraphysiologic Levels of Estrogen on Implantation:

There is controversy regarding the effect of ovarian hyperstimulation on endometrial development. Most investigators have reported adverse effects of high estrogen levels on endometrial development but there was no consensus on the actual mechanism of this effect. Endometrial biopsies for dating have shown both endometrial advancement and endometrial retardation in relation to high serum estradiol concentrations. However, all studies confirm direct effects on endometrial development that may jeopardize the chance of implantation due to the lack of synchronization between the endometrium and early embryo development. Such synchronization is crucial for successful implantation (window of implantation).

Various studies have shown a high incidence of endometrial glandular advancement[5] and retardation[6] using morphological and immunohistochemical criteria[7]. One study of natural versus ovarian stimulation cycles, demonstrated an advanced development of the ultrastructure of endometrial surface epithelium in the stimulation cycles[8]. However, another investigation demonstrated that ovulation induction was not associated with abnormal endometrial development[9].

More recently, the effect of excessively high estradiol concentrations (>20,000 pmol/L) were found to be associated with a deficient secretory transformation of the endometrium and a suboptimal endometrial environment for implantation. This finding supports clinical observations of significantly lower pregnancy rates in IVF cycles in women with estradiol concentrations ≧20,000 pmol/l. In these patients, there was a marked stromal oedema associated with a significantly greater number of vessels, and advanced stromal maturation possibly representing a direct effect of high estradiol levels on the endometrium[10]. In another study, an asynchronous development of endometrial glands and stromal was found in women undergoing IVF[11].

Most recently, a detrimental effect of high estrogen concentrations has been demonstrated on the embryo itself. Decreased blastocyst formation and reduce embryo adhesion to an endometrial cell layer was observed in the presence of elevated estrogen concentrations[12].

It appears that excessive estradiol production during controlled ovarian stimulation leads to insufficient secretory transformation of the endometrium and a discordant glandular and stromal development at a time that coincides with the period of maximum uterine receptivity. In addition, there are possible adverse effects directly oh the embryo that could reduce the chance for implantation. This may explain the findings of decreased implantation and pregnancy rates in IVF when serum estradiol concentrations are exceptionally high.

Measures to Improve Pregnancy Outcome by Reducing E2 Levels:

Different approaches have been suggested to improve the treatment outcome during assisted reproduction by reducing the intensity of ovarian stimulation to reduce the high estrogen levels. These approaches included minimal stimulation IVF cycles and natural cycle IVF which have been reported to be effective methods of treatment for ovulatory women undergoing assisted conception[13]. Other measures to lower estrogen levels include decreasing the FSH dose (step down protocol). With the use of a step-down FSH regimen in high responders, uterine receptivity may be improved secondary to lowering E2 levels during the preimplantation period[14]. Coasting or withholding FSH injections for a period of time prior to administration of hCG has been suggested in patients at substantial risk for the development of severe ovarian hyperstimulation syndrome (OHSS) and is associated with lowered estradiol levels[15]. However, all these measures are associated with the major drawback of decreasing the number of oocytes retrieved and embryos produced.

Aromatase Inhibition

As discussed above, the undesirable effects of ovarian stimulation on the outcome of infertility treatment may be due to the supraphysiologic levels of estrogen. Lowering estrogen levels may be associated with improved outcome by improving the implantation and pregnancy rates in addition to lowering risk of severe ovarian hyperstimulation syndrome. Reducing estrogen synthesis by aromatase inhibition during assisted reproductive technologies could be a way to ameliorate the deleterious effects of the supraphysiologic levels of estrogen during ovarian stimulation.

Until recently there was no effective aromatase inhibitor that could be used clinically to reduce estrogen levels during ovarian stimulation. This is because the available aromatase inhibitors (e.g. aminoglutethemide) lacked specificity to inhibit the aromatase enzyme without inhibiting other steroidogensis enzymes. The other aromatase inhibitors (steroidal androstenedione analogues) were irreversible in their effect on the aromatase enzyme and needed to be parentally administered. Most important, these old aromatase inhibitors were not potent enough to inhibit the aromatase and lower estrogen levels in women of the reproductive age group. A new group of non-steroidal aromatase inhibitors (letrozole, anastrazole and vorazole) is very potent and specific, reversibly inhibiting aromatase when orally administered with very high safety profile. Moreover, they have a relatively short half-life.

In Vitro Fertilization and In Vitro Maturation

It is useful to review in vitro fertilization and in vitro maturation for purposes of understanding the present invention. In vitro fertilization (IVF) in conventional use involves daily injections of fertility drugs, usually gonadotropins. Oocytes grow inside follicles and mature in the body. The mature oocytes are retrieved and fertilized by adding sperm in vitro in the laboratory.

In vitro maturation (IVM) does not necessarily involve the use of fertility drugs or may involve decreased doses of gonadotrophins when compared with IVF or OI. In the procedure, which is well documented in the literature, immature oocytes are retrieved from the female ovary at about day 7 for natural or artificial exogenous (gonadotrophins used) cycle and matured in vitro in the laboratory. Mature oocytes are then fertilized in the laboratory by intra-cytoplasmic sperm injection (ICSI). This procedure was developed for infertile women with polycystic ovary syndrome (PCOS). The advantages over in vitro fertilization (IVF) are reduced exposure to fertility drugs, reduced requirements for patient monitoring and because of the reduced exposure to fertility drugs, drug side effects are substantially eliminated, especially those associated with ovarian hyperstimulation syndrome (OHSS).

The procedure for IVM comprises the following steps:
Menstrual bleeding is induced by progestin.
Ultrasound (U/S) scan is performed on day 6-9 of the cycle.
Blood is drawn for maternal serum at time of U/S.
PCOS pattern of follicles without a dominant follicle (1.5 cm or greater) is seen at this time.
Human chorionic gonadotropin (hCG) 10,000 IU is given to the patient using vaginal ultrasound-guided needle aspiration and local anesthesia.
Egg retrieval 36 hours later and egg collection takes 15 to 30 minutes.
The harvested immature oocytes are cultured in maturation medium for 24 hours.
A fresh sperm sample from the female's partner is prepared for insemination.
The mature oocytes are then fertilized by ICSI.
Fertilization is checked at 16 hours after ICSI.
The fertilized oocytes are cultured for another 2 days.
Natural progesterone (Prometrium) is started vaginally (200 mg twice daily) on the day of oocyte insemination.
Two or three embryos (or one to two blastocysts) are transferred into the uterus.
Embryo transfer takes a few minutes and is painless.

SUMMARY OF THE INVENTION

Although aromatase inhibitors have not been used in women of the reproductive age group, we have discovered the effectiveness of these drugs, to decrease estrogen levels in women of the reproductive age group. Moreover, we found that estrogen levels following induction or augmentation of ovulation with aromatase inhibitors were significantly lower (especially serum E2 concentration/mature follicle) when compared with conventional stimulation protocols.

A reduction in E2 levels is beneficial in improving pregnancy outcome of assisted reproduction treatment. The use of aromatase inhibition reduces the supraphysiologic levels of estrogen during assisted reproductive technology cycles to improve the implantation and pregnancy rates in such cycles. As a result, fewer embryos need to be transferred to achieve a pregnancy thereby reducing the risk of multiple pregnancies. A reduction in E2 levels may also be beneficial in reducing the risk of ovarian hyperstimulation syndrome (OHSS).

Assisted Reproductive Technologies (ART)

Assisted reproductive technologies (ART) includes, for example, the following techniques:

In vitro fertilization (IVF), in which oocytes are aspirated from pre-ovulatory follicles, combined with sperm in vitro and viable embryos are selected and placed in the uterus.

Gamete Intrafallopian Transfer Procedure (GIFT), in which oocytes and sperm are combined in a catheter, and placed in the fallopian tube, so that conception occurs in the fallopian tube.

Zygote Intrafallopian Transfer Procedure (ZIFT), in which the collected oocytes are combined with sperm, and fertilized embryos are transferred to the fallopian tube.

Intracytoplasmic Sperm Injection (ICSI), in which each oocyte is directly injected With a single sperm via a microscopic needle, and viable embryos are selected for placement in the uterus or the fallopian tube.

Intrauterine insemination (IUI). Intrauterine insemination (IUI) is a fertility procedure in which motile sperm are washed, concentrated, and injected directly into a woman's uterus.

Therapeutic Donor insemination (TDI) involves the use of timed insemination of sperm from a donor rather than from the husband.

Controlled ovarian Hyperstimulation (COH) for timed intercourse, for IUI or for other ART procedures such as IVF encompasses the concept of deliberate and regulated induction of superovulation, but also refers to production of a hormonal response intended to lead to the production of multiple eggs in the woman's ovaries and to favor implantation of the embryo into the endometrium.

Thus, the present invention provides a method for improving the implantation and pregnancy rates for females undergoing assisted reproduction treatment (e.g. IVF, GIFT, ZIFT, ICSI, IUI, TDI and COH) or ovarian stimulation cycles for ovulation induction, which comprises administering to such females one or more daily doses of an aromatase inhibitor (AI) during assisted reproduction cycles or ovarian stimulation cycles, wherein the doses of AI are selected from amounts effective to reduce serum estradiol levels.

The invention also provides a method of increasing the production of follicles below the size of dominant follicles for the purpose of harvesting immature eggs for oocyte maturation in vitro by administration of one or more daily doses of at least one aromatase inhibitor to a female early in one or more menstrual cycles. Dominant follicles are generally more than 1.0 cm in diameter. Preferably this treatment eliminates the need for FSH treatment altogether and prevents the occurrence of ovarian hyperstimulation (OHSS). The AI is preferably administered as early as possible in the menstrual cycle so as to avoid having a negative impact on the developing embryo.

All patients undergoing COH with FSH suffer from high estrogen levels associated with higher follicle numbers, whether undergoing ovulation induction regimen or regimens for ART.

Preferably, from 1 to 10 daily doses of the aromatase inhibitor are administered. Most preferably, a total of 5 or fewer daily doses of the aromatase inhibitor are administered or a single dose of the AI is administered.

In another aspect the invention provides a method for improving the implantation and pregnancy rates for females undergoing assisted reproduction treatment which comprises administering a combination of one or more daily doses of at least one aromatase inhibitor (AI) with a plurality of daily doses of follicle stimulating hormone (FSH).

In some commercial forms of FSH, lutenizing hormone (LH) may also be present, and hence, the invention also encompasses daily doses of FSH and LH in place of daily doses of FSH alone. A particular example of such a mixed preparation is human menopausal gonadotrophin (hMG), which is a 1:1 mixture (I.U./I.U.) of FSH and LH.

Another aspect of the invention provides a pharmaceutical preparation for improving the implantation and pregnancy rates for females undergoing assisted reproduction treatment comprising one or more daily doses of a composition comprising an effective amount for improving the implantation and pregnancy rates for females of an aromatase inhibitor together with a pharmaceutically acceptable carrier.

The invention also provides for a two component pharmaceutical preparation for improving the implantation and pregnancy rates for females comprising one or more daily doses of an aromatase inhibitor together with a pharmaceutically acceptable carrier in combination with a plurality of daily doses of follicle stimulating hormone together with a pharmaceutically acceptable carrier.

Another aspect of the invention comprises a pharmaceutical preparation for increasing the production of follicles below the size of dominant follicles for the purpose of harvesting immature eggs for oocyte maturation in vitro which comprises one or more daily doses of at least one aromatase inhibitor together with a pharmaceutically acceptable carrier.

The invention also provides the use of one or more daily doses of an aromatase inhibitor either alone or in combination with a plurality of daily doses of follicle stimulating hormone for improving implantation and pregnancy rates for females, in ovarian stimulation for ovulation induction, in ART, and in a natural cycle.

The invention also provides for the use of one or more daily doses of at least one aromatase inhibitor in amounts effective to reduce serum estradiol levels for increasing the production of follicles below the size of dominant follicles for the purpose of harvesting immature eggs for oocyte maturation in vitro.

Another part of the invention comprises the use of one or more daily doses of an aromatase inhibitor in the preparation of a medicament for improving the implantation and pregnancy rates for females.

The use of an aromatase inhibitor during ovulation induction cycles and cycles for ART decreases the dose of FSH required.

In ART cycles in which the development of multiple follicles is stimulated with FSH or hMG (controlled ovarian hyperstimulation, COH), the high number of follicles causes estrogen levels to increase substantially. The increased estrogen levels may trigger the release of an LH surge from the pituitary. The sudden increase in LH levels may cause some developing follicles to luteinise and thus not yield oocytes. Other follicles may release their oocytes into the fallopian tubes, which is undesirable for ART cycles. (In ART cycles the oocytes are collected prior to release, by aspiration from the pre-ovulatory follicle.) In order to prevent such an LH surge, a GnRH agonist or GnRH antagonist is given to induce a state called down-regulation. The agonist or antagonist suppresses pituitary gonadotrophins, thus preventing an endogenous LH surge. This allows controlled timing for administering the hCG bolus and oocyte collection.

The inventors have found that estrogen levels can be decreased during stimulation with FSH or a mixture of FSH and LH, by administration of an aromatase inhibitor. Because of the decreased estrogen levels, an LH surge can be prevented. When aromatase activity is suppressed, estrogen levels remain within a normal range for a natural cycle in a healthy patient, or even below this level, at the level of a post-menopausal woman, or even below the level detectable with common immunoassays. Because of the lower estrogen levels, the pituitary will not respond with an LH surge. The use of an aromatase inhibitor can effectively replace the use of a GnRH agonist or antagonist in some patients.

While one aromatase inhibitor is preferred for use in the present invention, combinations of aromatase inhibitors may be used especially those of aromatase inhibitors having different half-lives. The aromatase inhibitor is preferably selected from aromatase inhibitors having a half-life of about 8 hours to about 4 days, more preferably from aromatase inhibitors having a half-life of about 2 days. Most beneficial are those aromatase inhibitors selected from non-steroidal and reversible aromatase inhibitors. More detail on the types of aromatase inhibitors that may be used in the methods, uses, preparations and packages of the present invention appears subsequently herein.

The aromatase inhibitors that have been found to be most useful of the commercially available forms are those in oral form. This form offers clear advantages over other forms, including convenience and patient compliance. Preferred aromatase inhibitors of those that are commercially available include anastrozole, letrozole, vorozole and exemestane. Exemestane (Aromasin™) is an example of a steroidal aromatase inhibitor that may be used in the present invention.

The daily doses required for the present invention depend on the type of aromatase inhibitor that is used. Some inhibitors are more active than others and hence lower amounts of such inhibitors could be used.

Typically, the amount of aromatase inhibitor for the improved implantation and pregnancy rates may be selected from amounts that lower estrogen levels to about normal physiological levels in a female such that serum estradiol concentration is less than at or about 10,000 pmol/L, preferably from at or about 300 to at or about 5000 pmol/L. in a female. In the case of increasing the production of follicles below the size of dominant follicles, the AI may be administered in amounts that lower estrogen levels to post menopausal levels in a female. For example the amount of aromatase inhibitor may be selected from amounts that lower the level of estrogen to at or about 100 pmol/L or less as measured by standard immunoassay techniques. These techniques are well known to those skilled in the art.

Examples of preferred suitable dosages are as follows. When the aromatase inhibitor is selected from anastrozole, letrozole and vorozole, the daily dose administered may be an amount in the range from at or about 1 mg to at or about 10 mg. When the aromatase inhibitor is exemestane, the amount administered in a daily dose may range from at or about 10 mg to at or about 200 mg. When the aromatase inhibitor is letrozole, it is preferably administered in a daily dose of from at or about 2.5 mg to at or about 10.0 mg. When the aromatase inhibitor is anastrozole, preferably, it is administered in a daily dose of from at or about 1 mg to at or about 4 mg. When the aromatase inhibitor is vorozole, the preferred daily dose is from at or about 2 to at or about 8 mg. Exemestane is preferably administered in a daily dose of at or about 25 to at or about 50 mg. Preferred are 1 to 10 daily doses of the aromatase inhibitor with administration starting on any of days 1 to 5 of the menstrual cycle. Most preferably the daily doses of the aromatase inhibitor comprise five daily doses. Most preferably the daily doses are administered sequentially.

In another preferred form of the invention a single dose of AI is administered in place of the multiple daily doses described above. The aromatase inhibitor is preferably administered in a single dose selected from amounts in the range of from at or about 5 mg to at or about 500 mg (e.g., at or about 10 mg, 20 mg, 25 mg or 30 mg to at or about 500 mg) and when the FSH is used, daily doses of follicle stimulating hormone range from at or about 25 to at or about 600 units (e.g., at or about 50 to at or about 225 units, e.g., to at or about 150 units) or an equivalent dosage in another form of administration.

The FSH used may be any of the commercially available products, including urinary and recombinant FSH. FSH may also be used in a form, which includes LH (Luteinizing Hormone).

The dosages for FSH may range from at or about 25 to at or about 600 units daily or its equivalent in other delivery forms with the period of administration being from about 1 to about 15 days. The FSH may be administered simultaneously, separately, sequentially, consecutively, with or without a gap or with some dosage overlap, with the AI.

Other types of ovulatory infertility which may be treated in accordance with the present invention may include endometriosis, cervical mucus abnormalities, older patients, (e.g. older than at or about 35, preferably younger than at or about 50, more preferably younger than at or about 45, most preferably at or about 38 to at or about 42) increased baseline FSH concentration, elevated FSH concentration, and low male sperm count (male factor infertility) requiring IUI (Intrauterine Insemination) or TDI (therapeutic donor insemination) in which augmenting ovulation in the female partner is indicated.

While female here is preferably a human being, the treatments may be applied to other species as appropriate.

Aromatase Inhibitor

By "aromatase inhibitors" there are to be understood substances that inhibit the enzyme aromatase (estrogen synthetase), which is responsible for converting androgens to estrogens.

Aromatase inhibitors may have a non-steroidal or a steroidal chemical structure. According to the present invention, both non-steroidal aromatase inhibitors and steroidal aromatase inhibitors can be used.

By aromatase inhibitors there are to be understood especially those substances that in a determination of the in vitro inhibition of aromatase activity exhibit $IC_{50}$ values of $10^{-5}$ M or lower; especially $10^{-6}$ M or lower, preferably $10^{-7}$ M or lower and most especially $10^{-8}$ M or lower.

The in vitro inhibition of aromatase activity can be demonstrated, for example, using the methods described in J. Biol. Chem. 249, 5364 (1974) or in J. Enzyme Inhib. 4, 169 (1990). In addition, $IC_{50}$ values for aromatase inhibition can be obtained, for example, in vitro by a direct product isolation method relating to inhibition of the conversion of $4\text{-}^{14}$ C-androstenedione to $4\text{-}^{14}$ C-oestrone in human placental microsomes.

By aromatase inhibitors there are to be understood most especially substances for which the minimum effective dose in the case of in vivo aromatase inhibition is 10 mg/kg or less, especially 1 mg/kg or less, preferably 0.1 mg/kg or less and most especially 0.01 mg/kg or less.

In vivo aromatase inhibition can be determined, for example, by the following method [see J. Enzyme Inhib. 4, 179 (1990)]: androstenedione (30 mg/kg subcutaneously) is administered on its own or together with an aromatase inhibitor (orally or subcutaneously) to sexually immature female rats for a period of 4 days. After the fourth administration, the rats are sacrificed and the uteri are isolated and weighed. The aromatase inhibition is determined by the extent to which the hypertrophy of the uterus induced by the administration of androstenedione alone is suppressed or reduced by the simultaneous administration of the aromatase inhibitor.

The following groups of compounds are listed as examples of aromatase inhibitors. Each individual group forms a group of aromatase inhibitors that can be used successfully in accordance with the present invention:

(a) The compounds of formulae I and I* as defined in EP-A-165 904. These are especially the compounds of formula I

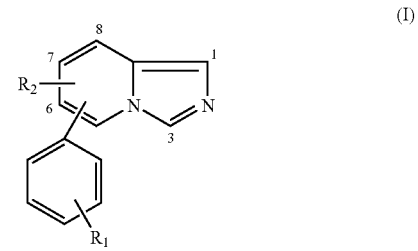

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, N-thiomorpholino, N-piperazino piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2\text{-}C_7$ alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and the compounds of formula I*

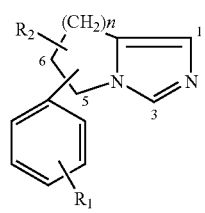

(I*)

wherein n is 0, 1, 2, 3 or 4; and $R_1$ and $R_2$ are as defined above for formula I; it being possible for the phenyl ring in the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or by halogen; it being possible in a compound of formula I* for the two substituents $C_6H_4$—$R_1$ and $R_2$ to be linked to each of the saturated carbon atoms of the saturated ring, either both to the same carbon atom or both to different carbon atoms, and pharmaceutically acceptable salts thereof.

Individual compounds that may be given special mention here are:

(1) 5-(p-cyanophenyl)imidazo[1,5-a]pyridine,
(2) 5-(p-ethoxycarbonylphenyl)imidazo[1,5-a]pyridine,
(3) 5-(p-carboxyphenyl)imidazol[5-a]pyridine,
(4) 5-(p-tert-butylaminocarbonylphenyl)imidazo[1,5-a]pyridine,
(5) 5-(p-ethoxycarbonylphenyl)-5,6,7,8-tetrahydroimidazo[1,5-a]pyridine,
(6) 5-(p-carboxyphenyl)-5,6,7,8-tetrahydroimidazo[1,5-a]pyridine,
(7) 5-(p-carbamoylphenyl)-5,6,7,8-tetrahydroimidazo[1,5-a]pyridine,
(8) 5-(p-tolyl)-5,6,7,8-tetrahydroimidazo[1,5-a]pyridine,
(9) 5-(p-hydroxymethylphenyl)imidazo[1,5-a]pyridine,
(10) 5-(p-cyanophenyl)-7,8-dihydroimidazo[1,5-a]pyridine,
(11) 5-(p-bromophenyl)-5,6,7,8-tetrahydroimidazo[1,5-a]pyridine,
(12) 5-(p-hydroxymethylphenyl)5,6,7,8-tetrahydroimidazo[1,5-a]pyridine,
(13) 5-(p-formylphenyl)-5,6,7,8-tetrahydroimidazo[1,5-a]pyridine,
(14) 5-(p-cyanophenyl)-5-methylthio-5,6,7,8-tetrahydroimidazo[1,5-a]pyridine,
(15) 5-(p-cyanophenyl)-5-ethoxycarbonyl-5,6,7,8-tetrahydroimidazo[1,5-a]pyridine,
(16) 5-(p-aminophenyl)-5,6,7,8-tetrahydroimidazo[1,5-a]pyridine,
(17) 5-(p-formylphenyl)imidazo[1,5-a]pyridine,
(18) 5-(p-carbamoylphenyl)imidazo[1,5-a]pyridine,
(19) 5H-5-(4-tert-butylaminocarbonylphenyl)-6,7-dihydropyrrolo[1,2-c]imidazole,
(20) 5H-5-(4-cyanophenyl)-6,7-dihydropyrrolo[1,2]imidazole,
(21) 5H-5-(4-cyanophenyl)-6,7,8,9-tetrahydroimidazo[1,5-a]azepine,
(22) 5-(4-cyanophenyl)-6-ethoxycarbonylmethyl-5,6,7,8-tetrahydroimidazo[1,5-a]pyridine,
(23) 5-(4-cyanophenyl)-6-carboxymethyl-5,6,7,8-tetrahydroimidazo[1,5-a]pyridine
(24) 5-benzyl-5-(4-cyanophenyl)-5,6,7,8-tetrahydroimidazo[1,5-a]pyridine,
(25) 7-(p-cyanophenyl)-5,6,7,8-tetrahydroimidazo[1,5-a]pyridine,
(26) 7-(p-carbamoylphenyl)-5,6,7,8-tetrahydroimidazo[1,5-a]pyridine,
(27) 5-(p-cyanophenyl)5,6,7,8-tetrahydroimidazo[1,5-a]pyridine (=Fadrozol).

(b) The compounds of formula I as defined in EP-A 236 940. These are especially the compounds of formula I

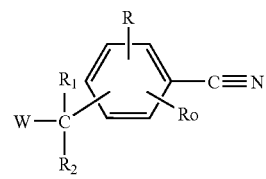

(I)

wherein R and $R_0$, independently of one another, are each hydrogen or lower alkyl, or R and $R_0$ at adjacent carbon atoms, together with the benzene ting to which they are bonded, form a naphthalene or tetrahydronaphthalene ring; wherein $R_1$ is hydrogen, lower alkyl, aryl, aryl-lower alkyl or lower alkenyl; $R_2$ is hydrogen, lower alkyl, aryl, aryl-lower alkyl, (lower alkyl, aryl or aryl-lower alkyl)-thio or lower alkenyl, or wherein $R_1$ and $R_2$ together are lower alkylidene or $C_4$-$C_6$ alkylene; wherein W is 1-imidazolyl, 1-(1,2,4 or 1,3,4)-triazolyl, 3-pyridyl or one of the mentioned heterocyclic radicals substituted by lower alkyl; and aryl within the context of the above definitions has the following meanings: phenyl that is unsubstituted or substituted by one or two substituents from the group lower alkyl, lower alkoxy, hydroxy, lower alkanoyloxy, nitro, amino, halogen, trifluoromethyl, cyano, carboxy, lower alkoxycarbonyl, carbamoyl, N-lower alkylcarbamoyl, N,N-di-lower alkylcarbamoyl, lower alkanoyl, benzoyl, lower alkylsulfonyl, sulfamoyl, N-lower alkylsulfamoyl and N,N-di-lower alkylsulfamoyl; also thienyl, indolyl, pyridyl or furyl, or one of the four last-mentioned heterocyclic radicals monosubstituted by lower alkyl, lower alkoxy, cyano or by halogen; and pharmaceutically acceptable salts thereof.

Individual compounds from that group that may be given special mention are:

(1) 4-[alpha-(4-cyanophenyl)-1-imidazolylmethyl]-benzonitrile,
(2) 4-[alpha-(3-pyridyl)-1-imidazolylmethyl]-benzonitrile,
(3) 4-[alpha-(4-cyanobenzyl)-1-imidazolylmethyl]-benzonitrile,
(4) 1-(4-cyanophenyl)-1-(1-imidazolyl)-ethylene,
(5) 4-[alpha-(4-cyanophenyl)-1-(1,2,4-triazolyl)methyl]-benzonitrile,
(6) 4-[alpha-(4-cyanophenyl)-3-pyridylmethyl]-benzonitrile.

(c) The compounds of formula I as defined in EP-A408 509. These are especially the compounds of formula I

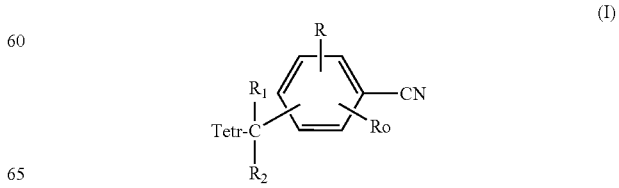

(I)

wherein Tetr is 1- or 2-tetrazolyl that is unsubstituted or substituted in the 5-position by lower alkyl, phenyl-lower alkyl or by lower alkanoyl; R and $R_2$, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$-$C_6$ cycloalkyl, $C_3$-$C_6$ cycloalkyl-lower alkyl, lower alkylthio, arylthio or aryl-lower alkylthio; or $R_1$ and $R_2$ together are straight-chained $C_4$-$C_6$ alkylene that is unsubstituted or substituted by lower alkyl, or are a group —$(CH_2)_m$-1,2-phenylene-$(CH_2)_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below; aryl in the above definitions being phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; heteroaryl in the above definitions being an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above; and pharmaceutically acceptable salts thereof.

Individual compounds from that group that may be given special mention are:
(1) 4-(2-tetrazolyl)methyl-benzonitrile,
(2) 4-[α-(4-cyanophenyl)-(2-tetrazolyl)methyl]-benzonitrile,
(3) 1-cyano-4-(1-tetrazolyl)methyl-naphthalene,
(4) 4-[α-(4-cyanophenyl)(1-tetrazolyl)methyl]-benzonitrile.

(d) The compounds of formula I as defined in European Patent Application No. 91810110.6. These are especially the compounds of formula I

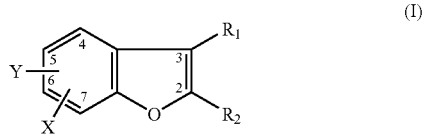

wherein X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen and/or by trifluoromethyl; Y is a group —$CH_2$-A wherein A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl, or Y is hydrogen, $R_1$ and $R_1$, independently of one another, are each hydrogen, lower alkyl or a group —$CH_2$-A as defined for Y, or $R_1$ and $R_2$ together are —$(CH_2)_n$— wherein n is 3, 4 or 5, with the proviso that one of the radicals Y, $R_1$ and $R_2$ is a group —$CH_2$-A, with the further proviso that in a group —$CH_2$-A as a meaning of $R_1$ or $R_2$, A is other than 1-imidazolyl when X is bromine, cyano or carbamoyl, and with the proviso that in a group —$CH._2$-A as a meaning of Y, A is other than 1-imidazolyl when X is halogen or lower alkoxy, $R_1$ is hydrogen and $R_2$ is hydrogen or lower alkyl, and pharmaceutically acceptable salts thereof.

Individual compounds from that group that may be given special mention are:
(1) 7-cyano-4-[1-(1,2,4-triazolyl)methyl]-2,3-dimethylbenzofuran,
(2) 7-cyano-4-(1-imidazolylmethyl)-2,3-dimethylbenzofuran,
(3) 7-carbamoyl-4-(1-imidazolylmethyl 2,3-dimethylbenzofuran,
(4) 7-N-(cyclohexylmethyl)carbamoyl-4-(1-imidazolylmethyl)-2,3-dimethylbenzofuran.

(e) The compounds of formula I as defined in Swiss Patent Application 1339/90-7.

These are especially the compounds of formula I

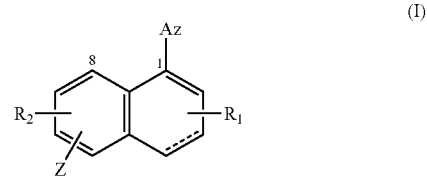

wherein the dotted line denotes an additional bond or no additional bond, Az is imidazolyl, triazolyl or tetrazolyl bonded via a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and $R_1$ and $R_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and pharmaceutically acceptable salts thereof.

Individual compounds from that group that may be given special mention are:
(1) 6-cyano-1-(1-imidazolyl)-3,4-dihydronaphthalene,
(2) 6-cyano-1-[1-(1,2,4-triazolyl)]-3,4-dihydronaphthalene,
(3) 6-chloro-1-(1-imidazolyl)-3,4-dihydronaphthalene,
(4) 6-bromo-1-(1-imidazolyl)-3,4-dihydronaphthalene.

(f) The compounds of formula I as defined in Swiss Patent Application 3014/90-0.

These are especially the compounds of formula I

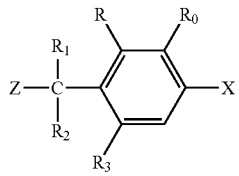

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —(CH$_2$)$_3$—; or $R_1$ and $R_2$ and $R_3$ together are a group =CH—(CH$_2$)$_2$— wherein the single bone is linked to the benzene ring; X is cyano; and X may also be halogen when $R_2$ and $R_3$ together are —(CH$_2$)$_3$— or $R_1$ and $R_1$ and $R_3$ together are a group =CH—(CH$_2$)$_2$—; and pharmaceutically acceptable salts thereof.

Individual compounds from that group that may be given special mention are:
(1) 4-[α-(4-cyanophenyl)-α-hydroxy-5-isothiazolylmethyl]-benzonitrile.
(2) 4-[α-(4-cyanophenyl)-5-isothiazolylmethyl]-benzonitrile,
(3) 4-[α-(4-cyanophenyl)-5-thiazolylmethyl]-benzonitrile,
(4) 1-(4-cyanophenyl)-1-(5-thiazolyl)-ethylene,
(5) 6-cyano-1-(5-isothiazolyl)-3,4-dihydronaphthalene,
(6) 6-cyano-1-(5-thiazolyl)-3,4-dihydronaphthalene.

(g) The compounds of formula VI as defined in Swiss Patent Application 3014/90-0.

These are especially the compounds of formula VI

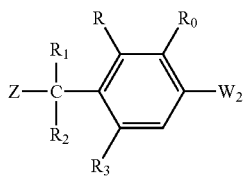

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl). 5-(1,2,3-oxadiazolyl) 3-(1,2,5-thiadiazolyl), 3-(1,2,5-oxadiazolyl), 4-isothiazolyl. 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are each hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene, and $W_2$ is halogen, hydroxy, lower alkoxy, aryl-lower alkoxy or aryloxy; aryl in each case being phenyl that is unsubstituted or substituted by lower alkyl, lower alkoxy, hydroxy, halogen or by trifluoromethyl; and pharmaceutically acceptable salts thereof.

Individual compounds from that group that may be given special mention are:
(1) bis(4,4'-bromophenyl)-(5-isothiazolyl)methanol,
(2) bis(4,4'-bromophenyl)-(5-isothiazolyl)methane,
(3) bis(4,4'-bromophenyl)-(5-thiazolyl)methanol,
(4) bis(4,4'-bromophenyl)-(5-thiazolyl)methane, (h) The compounds of formula I as defined in Swiss Patent Application 3923/90-4.

These are especially the compounds of formula I

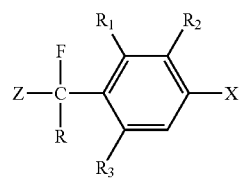

wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl. triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl: $R_1$ and $R_2$, independently of one another, are each hydrogen or lower alkyl; or $R_1$ and $R_2$ together are $C_3$-$C_4$ alkylene, or a benzo group that is unsubstituted or substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl) carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, N-hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoindolyl, benzimidazolyl, benzopyrazolyl or benzotriazolyl; wherein aryl is phenyl or naphthyl, these radicals being unsubstituted or substituted by from 1 to 4 substituents from the group consisting of lower alkyl, lower alkenyl, lower alkynyl, lower alkylene (linked to two adjacent carbon atoms), $C_3$-$C_8$ cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$-$C_8$ cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"— (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl lower alkylcarbamoyl, N-hydroxycarbamoyl, N-phenyl-lower alkylcarbamoyl, N-phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen and/or by trifluoromethyl; wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl; and pharmaceutically acceptable salts thereof.

Those compounds are especially the compounds of formula I whereto Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidyl, 5-pyrimidinyl or 2-pyrazinyl; $R_1$ and $R_2$, independently of one another, are each hydrogen or lower alkyl; or $R_{-1}$ and $R_2$ together are 1,4-butylene or a benzo group; R is lower alkyl; phenyl that is unsubstituted or substituted by cyano, carbamoyl, halogen, lower alkyl, trifluoromethyl, hydroxy, lower alkoxy or by phenoxy; or benzotriazolyl or benzo[b]furanyl, the last two radicals being unsubstituted or substituted by from 1 to 3 identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl 2-tetrazolyl; and pharmaceutically acceptable salts thereof.

Individual compounds that may be given special mention here are:

(1)  4-[α-4-cyanophenyl)-α-fluoro-1-(1,2,4-triazolyl)methyl]-benzonitrile,
(2)  4-[α-(4-cyanophenyl)-α-fluoro-(2-tetrazolyl)methyl]-benzonitrile,
(3)  4-[α-(4-cyanophenyl)-α-fluoro-(1-tetrazolyl)methyl]-benzonitrile,
(4)  4-[α-(4-cyanophenyl)-α-fluoro-(1-imidazolyl)methyl]-benzonitrile,
(5) 1-methyl-6-[α-(4-chlorophenyl)-α-fluoro-1-(1,2,4-triazolyl)methyl]-benzotriazole,
(6)  4-[α-(4-cyanophenyl)-α-fluoro-1-(1,2,3-triazolyl)methyl]-benzo nitrile,
(7)  7-cyano-4-[α-(4-cyanophenyl)-α-fluoro-1-(1,2,4-triazolyl)methyl]-2,3-dimethylbenzo[b]furan,
(8)  4-[α-(4-bromophenyl)-α-fluoro-1-(1,2,4-triazolyl)methyl]-benzo nitrile,
(9)  4-[α-(4-cyanophenyl)-α-fluoro-(5-pyrimidyl)methyl]-benzonitrile,
(10) 4-[α-(4-bromophenyl)-α-fluoro-(5-pyrimidyl)methyl]-benzonitrile,
(11)  4-[α-(4-cyanophenyl)-α-fluoro-(3-pyridyl)methyl]-benzonitrile,
(12)  7-bromo-4-[α-(4-cyanophenyl)-α-fluoro-(1-imidazolyl)methyl]-2,3-dimethylbenzo[b]furan,
(13) 7-bromo-4-[α-(4-cyanophenyl)-α-fluoro-1-(1,2,4-triazolyl)methyl-]-2,3-dimethylbenzo[b]furan,
(14)  4-[α-(4-cyanophenyl)-α-fluoro-(5-pyrimidyl)methyl)-benzonitrile,
(15) 4-[α-(4-bromophenyl)-α-fluoro-(5-pyrimidyl)methyl]-benzonitrile,
(16)  4-[α-(4-cyanophenyl)-1-(1,2,3-triazolyl)methyl]-benzonitrile,
(17)  2,3-dimethyl-4-[α-(4-cyanophenyl)-1-(1,2,4-triazolyl) methyl]-7-cyano-benzo[b]furan,
(18)  4-[α-(4-cyanophenyl)-(5-pyrimidyl)methyl]-benzonitrile,
(19)  4-[α-(4-bromophenyl)-(5-pyrimidyl)methyl]-benzonitrile,
(20) 2,3-dimethyl-4-[α-(4-cyanophenyl)-(1-imidazolyl)methyl]-7-bromo-benzo[b]furan,
(21)  2,3-dimethyl-4-[α-(4-cyanophenyl)-1-(1,2,4-triazolyl) methyl]-7-bromo-benzo-[b]furan.

(i) The compounds of formula I as defined in EP-A-114 033. These are especially the compounds of formula I

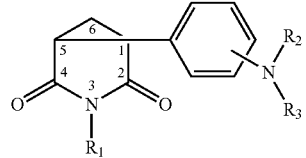

wherein $R_1$ is hydrogen, $R_2$ is hydrogen, sulfo, $C_1$-$C_7$ alkanoyl or $C_1$-$C_7$ alkanesulfonyl and $R_3$ is hydrogen, or wherein $R_1$ is $C_1$-$C_{12}$ alkyl, $C_{-2}$-$C_{12}$ alkenyl, $C_2$-$C_7$ alkynyl, $C_3$-$C_{10}$ cycloalkyl, $C_3$-$C_{-10}$ cycloalkenyl, $C_{-3}$-$C_6$ cycloalkyl-$C_1$-$C_4$ alkyl, $C_3$-$C_6$ cycloalkyl-$C_{-2}$-$C_4$ alkenyl or $C_3$-$C_6$ cycloalkenyl-$C_1$-$C_4$ alkyl, $R_2$ is hydrogen, $C_1$-$C_7$ alkyl, sulfo, $C_1$-$C_7$ alkanoyl or $C_1$-$C_7$ alkanesulfonyl and $R_3$ is hydrogen or $C_1$-$C_7$ alkyl, and salts of those compounds.

Individual compounds from that group that may be given special mention are:

(1)  1-(4-aminophenyl)-3-methyl-3-azabicyclo[3.1.0]hexane-2,4-dione,
(2)  1-(4-aminophenyl)-3-n-propyl-3-azabicyclo[3.1.0]hexane-2,4-dione,
(3)  1-(4-aminophenyl)-3-isobutyl-3-azabicyclo[3.1.0]hexane-2,4-dione,
(4)  1-(4-aminophenyl)-3-n-heptyl-3-azabicyclo[3.1.0]hexane-2,4-dione,
(5)  1-(4-aminophenyl)-3-cyclohexylmethyl-3-azabicyclo [3.1.0]hexane-2,4-dione.

(j) The compounds of formula I as defined in EP-A-166 692. These are especially the compounds of formula I

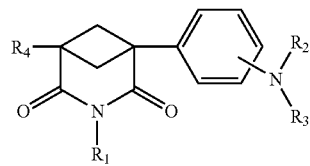 (I)

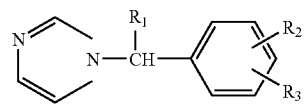 (I/Ia)

wherein R₁ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino amino or by halogen, R₂ is hydrogen, lower alkyl, sulfo, lower alkanoyl or lower alkanesulfonyl, sulfonyl, R₃ is hydrogen or lower alkyl and R₄ is hydrogen, lower alkyl, phenyl or phenyl substituted by —N(R₂)(R₃), and salts thereof, radicals described as "lower" containing up to and including 7 carbon atoms.

Individual compounds from that group that may be given special mention are:
(1) 1-(4-aminophenyl)-3-n-propyl-3-azabicyclo[3.1.1]heptane-2,4-dione,
(2) 1-(4-aminophenyl)-3-methyl-3-azabicyclo[3.1.1]heptane-2,4-dione,
(3) 1-(4-aminophenyl)3-n-decyl-3-azabicyclo[3.1.1]heptane-2,4-dione,
(4) 1-(4-aminophenyl)-3-cyclohexyl-3-azabicyclo[3.1.1]heptane-2,4-dione,
(5) 1-(4-aminophenyl)-3-cyclohexylmethyl-3-azabicyclo[3.1.1]heptane-2,4-dione.

(k) The compounds of formula I as defined in EP-A-356 673. These are especially the compounds of formula I

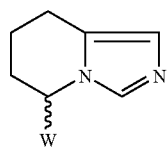 (I)

wherein W (α) is a 2-naphthyl or 1-anthryl radical, wherein each benzene ring is unsubstituted or substituted by a substituent selected from halogen, hydroxy, carboxy, cyano and nitro; or (.beta.) is 4-pyridyl, 2-pyrimidyl or 2-pyrazinyl, each of those radicals being unsubstituted or substituted by a substituent selected from halogen, cyano, nitro, $C_1$-$C_4$ alkoxy and $C_2$-$C_5$ alkoxycarbonyl; and pharmaceutically acceptable salts thereof.

Individual compounds from that group that may be given special mention are:
(1) 5-(2'-naphthyl)-5,6,7,8-tetrahydroimidazo[1,5-a]pyridine,
(2) 5-(4'-pyridyl)-5,6,7,8-tetrahydroimidazo[1,5-a]pyridine.

(l) The compounds of formula I or Ia as defined in EP-A-337 929. These are especially the compounds of formula I/Ia wherein R₁ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, R₂ is benzyloxy, 3-bromo-, 4-bromo-, 4-chloro-, 2,3-, 2,4-, 4,5- or 4,6-dichloro-benzyloxy, and R₃ is cyano; $C_2$-$C_{10}$ alkanoyl that is unsubstituted or mono- or poly-substituted by halogen, methoxy, amino, hydroxy and/or by cyano; benzoyl that is unsubstituted or substituted by one or more substituents from the group halogen, $C_1$-$C_4$ alkyl, methoxy, amino, hydroxy and cyano; carboxy, (methoxy, ethoxy or butoxy)-carbonyl, carbamoyl, N-isopropylcarbamoyl, N-phenylcarbamoyl, N-pyrrolidylcarbonyl, nitro or amino; and salts thereof.

Individual compounds from that group that may be given special mention are:
(1) 4-(2,4-dichlorobenzyloxy)-3-[1-(1-imidazolyl)-butyl]-benzonitrile,
(2) (4-(4-bromobenzyloxy)-3-[1-(1-imidazolyl)butyl]-phenyl pentyl ketone,
(3) 4-(4-bromobenzyloxy)-3-[1-(1-imidazolylybutyl)-benzanilide,
(4) 4-(4-bromobenzyloxy)-3-[1-(1-imidazolyl)-butyl]-benzoic acid,
(5) 3-(2,4-dichlorobenzyloxy)-4-[1-(1-imidazolyl)butyl]-benzonitrile,
(6) 3-(2,4-dichlorobenzyloxy)-4-[1-(1-imidazolyl)-butyl]-benzoic acid methyl ester,
(7) 3-(2,4-dichlorobenzyloxy)-4-[1-(1-imidazolyl)-butyl]-benzoic acid,
(8) 3-(3-bromobenzyloxy)-4-[1-(1-imidazolyl)-butyl]-benzonitrile,
(9) 4-(3-bromobenzyloxy)-3-[1-(1-imidazolyl)-butyl]-benzonitrile,
(10) 3-(4-bromobenzyloxy)-4-[1-(1-imidazolyl)-butyl]-benzoic acid,
(11) 3-(4-bromobenzyloxy)-4-[1-(1-imidazolyl)-butyl]-benzanilide,
(12) 3-(4-bromobenzyloxy)-4-[1-(1-imidazolyl)-butyl]-phenyl pentyl ketone,
(13) 4-(4-bromobenzyloxy)-3-[1-(1-imidazolyl)-butyl]-benzonitrile,
(14) 3-(4-bromobenzyloxy)-4-[1-(1-imidazolyl)-butyl]-benzonitrile,
(15) 4-nitro-2-[1-(1-imidazolyl)-butyl]-phenyl-(2,4-dichlorobenzyl)ether,
(16) 4-amino-2-[1-(1-imidazolyl)-butyl]-phenyl-(2,4-dichlorobenzyl)ether,
(17) (2,4-dichlorobenzyl)-[2-(1-imidazolyl-methyl)-4-nitrophenyl]ether.

(m) The compounds of formula I as defined in EP-A-337 928. These are especially the compounds of formula I

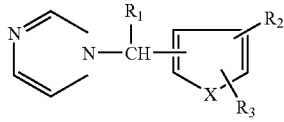

wherein R₁ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, N-isopropylcarbamoyl, N-phenylcarbamoyl, N-pyrrolidylcarbonyl; $C_2$-$C_{10}$ alkanoyl that is unsubstituted or mono- or poly-substituted by halogen, methoxy, ethoxy, amino, hydroxy and/or by cyano; or benzoyl that is unsubstituted or substituted by one or more substituents from the group halogen, $C_1$-$C_4$ alkyl, methoxy, ethoxy, amino, hydroxy and cyano, $R_3$ is hydrogen, benzyloxy, 3-bromo-, 4-bromo-, 4-chloro-, 2,3-, 2,4-, 4,5- or 4,6-dichlorobenzyloxy, and X is —CH═N—; —CH═N(—O)— or —S—; and salts thereof.

Individual compounds from that group that may be given special mention are:
(1) 5-[1-(1-imidazolyl)-butyl]-thiophene-2-carbonitrile,
(2) 2-[1-(1-imidazolyl)-butyl]-thiophene-4-carbonitrile,
(3) 2-[1-(1-imidazolyl)-butyl]-4-bromo-thiophene,
(4) 2-[1-(1-imidazolyl)-butyl]-5-bromo-thiophene,
(5) 5-[1-(1-imidazolyl)-butyl]-2-thienyl pentyl ketone,
(6) 5-[1-(1-imidazolyl)-butyl]-2-thienyl ethyl ketone,
(7) 5-(4-chlorobenzyloxy)-4-[1-(1-imidazolyl)-pentyl]-pyridine-2-carbonitrile,
(8) 3-(4-chlorobenzyloxy)-4-[1-(1-imidazolyl)-pentyl]-pyridine-2-carbonitrile,
(9) 3-(4-chlorobenzyloxy)-4-[1-(1-imidazolyl)-pentyl]-pyridine-N-oxide,
(10) 3-(4-chlorobenzyloxy)-4-[1-(1-imidazolyl)-pentyl]-pyridine.

(n) The compounds of formula I as defined in EP-A-340 153. These are especially the compounds of formula I

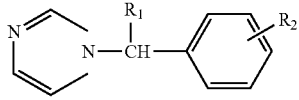

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, and $R_2$ is a radical from the group methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; or $R_2$ is formyl or derivatised formyl that can be obtained by reaction of the formyl group with an amine or amine derivative from the group hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents from the group halogen, $C_1$-$C_4$-alkyl, methoxy, amino, hydroxy and cyano; carboxy, (methoxy, ethoxy or butoxy)carbonyl, carbamoyl, N-isopropylcarbamoyl, N-phenylcarbamoyl or N-pyrrolidylcarbonyl; and salts thereof.

Individual compounds from that group that may be given special mention are:
(1) 4-(1-(1-imidazolyl)-butyl)-benzoic acid methyl ester,
(2) 4-(1-imidazolyl)-butyl)-benzoic acid butyl ester,
(3) 4-(1-(1-imidazolyl)-butyl)-phenyl-acetonitrile,
(4) 4-(1-(1-imidazolyl)-butyl)-benzaldehyde,
(5) 4-(1-(1-imidazolyl)-butyl)-benzyl alcohol,
(6) {4-[1-(1-imidazolyl)-butyl]-phenyl}-2-propyl ketone,
(7) 4-[1-(1-imidazolyl)-butyl]-phenyl propyl ketone,
(8) 4-[1-(1-imidazolyl)-butyl]-phenyl butyl ketone,
(9) 4-[1-(1-imidazolyl)-butyl]-phenyl pentyl ketone,
(10) 4-[1-(1-imidazolyl)-butyl]-phenyl hexyl ketone.

(o) The compounds of formula I as defined in DE-A-4 014 006. These are especially the compounds of formula I

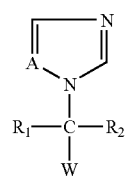

wherein A is an N-atom or a CH radical and W is a radical of the formula

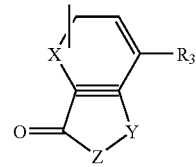

wherein X is an oxygen or a sulfur atom or a —CH═CH— group and Y is a methylene group, an oxygen or a sulfur atom and Z is a —$(CH_2)_n$— group wherein n=1, 2 or 3 and either a) $R_3$ in W is a hydrogen atom and $R_1$ and $R_2$, independently of one another, are each a hydrogen atom, a $C_1$— to $C_{10}$ alkyl group or a $C_3$— to $C_7$ cycloalkyl group, or b) $R_2$ is as defined under a) and $R_1$ together with $R_3$ forms a —$(CH_2)_m$— group wherein m=2, 3, or 4, and their pharmaceutically acceptable addition salts with acids.

Individual compounds from that group that may be given special mention are:
(1) 5-[1-(1-imidazolyl)-butyl]-1-indanone,
(2) 7-[1-(1-imidazolyl)-butyl]-1-indanone,
(3) 6-[1-(1-imidazolyl)-butyl]-1-indanone,
(4) 6-(1-imidazolyl)-6,7,8,9-tetrahydro-1H-benz[e]inden-3 (2H)-one,
(5) 2-[1-(1-imidazolyl)-butyl]-4,5-dihydro-6-oxo-cyclopenta[b]-thiophene,
(6) 6-[1-(1-imidazolyl)-butyl]-3,4-dihydro-2H-naphthalen-1-one,
(7) 2-[1-(1-imidazolyl)-butyl]-6,7-dihydro-5H-benzo[b] thiophen-4-one,
(8) 6-[1-(1-imidazolyl)-butyl]-2H-benzo[b]furan-3-one,
(9) 5-[cyclohexyl-(1-imidazolyl)-methyl]-1-indanone,

(10) 2-[1-(1-imidazolyl)-butyl]-4,5-dihydro-6H-benzo[b]thiophen-7-one,

(11) 5-[1-(1-imidazolyl)-1-propyl-butyl]-1-indanone,

(12) 2-[1-(1-imidazolyl)-butyl]-4,5-dihydro-6H-benzo[b]thiophen-7-one,

(13) 2-[1-(1-imidazolyl)butyl]-4,5-dihydro-6-oxo-cyclopenta[b]-thiophene,

(14) 5-(1-imidazolylmethyl)-1-indanone,

(15) 5-[1-(1,2,4-triazolyl)-methyl]-1-indanone.

(p) The compounds of formula I as disclosed in DE-A-3 926 365. These are especially the compounds of formula I

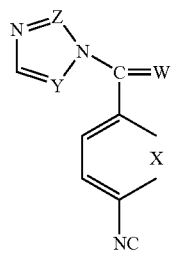

wherein W' is a cyclopentylidene, cyclohexylidene, cycloheptylidene or 2-adamantylidene radical, X is the grouping —CH=CH—, an oxygen or a sulfur atom, and Y and Z, independently of one another, are each a methine group (CH) or a nitrogen atom, and their pharmaceutically acceptable addition salts with acids.

Individual compounds from that group that may be given special mention are:

(1) 4-[1-cyclohexylidene-1-(imidazolyl)methyl]-benzonitrile, (2) 4-[1-cyclopentylidene-1-(imidazolyl)-methyl]-benzonitrile, (3) 4-[1-cycloheptylidene-1-(imidazolyl)-methyl]-benzonitrile, (4) 4-[2-adamantylidene-1-(imidazolyl)-methyl]-benzonitrile, (5) 4-[1-cyclohexylidene-1-(1,2,4-triazolyl)-methyl]-benzonitrile, (6) 4-[1-cyclopentylidene-1-(1,2,4-triazolyl)-methyl]-benzonitrile, (7) 4-[1-cycloheptylidene-1-(1,2,4-triazolyl)-methyl]-benzonitrile, (8) 4-[2-adamantylidene-1-(1,2,4-triazolyl)-methyl]-benzonitrile, (9) 4-[1-cyclohexylidene-1-(1,2,3-triazolyl)-methyl]-benzonitrile,

(10) 4-[1-cyclopentylidene-1-(1,2,3-triazolyl)-methyl]-benzonitrile,

(11) 5-[cyclohexylidene-1-imidazolylmethyl]-thiophene-2-carbonitrile.

(q) The compounds of formula I as defined in DE-A-3 740 125. These are especially the compounds of formula I

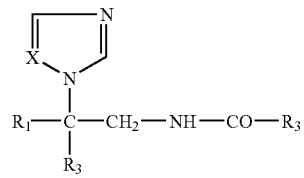

wherein X is CH or N, $R_1$ and $R_2$ are identical or different and are each phenyl or halophenyl, and $R_3$ is $C_1$-$C_4$ alkyl; $C_1$-$C_4$ alkyl substituted by CN, $C_1$-$C_4$ alkoxy, benzyloxy or by $C_1$-$C_4$ alkoxy-(mono-, di- or tri-)ethyleneoxy; $C_1$-$C_4$ alkoxy, phenyl; phenyl that is substituted by halogen or by cyano; a $C_5$-$C_7$ cycloalkyl group that is optionally condensed by benzene, or is thienyl, pyridyl or 2- or 3-indolyl; and acid addition salts thereof.

An individual compound from that group that may be given special mention is:

(1) 2,2-bis(4-chlorophenyl)-2-(1H-imidazol-1-yl)-1-(4-chlorobenzoyl-amino) ethane.

(r) The compounds of formula I as defined in EP-A-293 978. These are especially the compounds of formula I

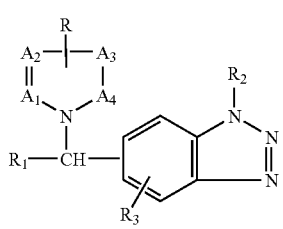

pharmaceutically acceptable salts and stereochemically isomeric forms thereof, wherein -$A_1$=$A_2$-$A_3$=$A_4$- is a divalent radical selected from —CH=N—CH=CH—, —CH=N—CH=N— and —CH=N—N=CH—. R is hydrogen or $C_1$-$C_6$ alkyl; $R_1$ is hydrogen, $C_1$-$C_{10}$ alkyl, $C_3$-$C_7$ cycloalkyl. $Ar_1$, $Ar_2$—$C_1$-$C_6$ alkyl, $C_2$-$C_6$ alkenyl or $C_2$-$C_6$ alkynyl: $R_2$ is hydrogen; $C_1$-$C_{10}$ alkyl that is unsubstituted or substituted by $Ar_1$; $C_3$-$C_7$ cycloalkyl, hydroxy, $C_1$-$C_6$ alkoxy, $Ar_1$, $C_2$-$C_6$ alkenyl, $C_2$-$C_6$ alkynyl, $C_3$-$C_7$ cycloalkyl, bicyclo[2.2.1]heptan-2-yl, 2,3-dihydro-1H-indenyl, 1,2,3,4-tetrahydronaphthyl, hydroxy; $C_2$-$C_6$ alkenyloxy that is unsubstituted or substituted by $Ar_2$; $C_2$-$C_6$ alkynyloxy; pyrimidyloxy; di($Ar_2$) methoxy, (1-$C_1$-$C_4$ alkyl-4-piperidinyl)oxy, $C_1$-$C_{10}$ alkoxy; or $C_1$-$C_{10}$ alkoxy that is substituted by halogen, hydroxy, $C_1$-$C_6$ alkyloxy, amino, mono- or di-($C_1$-$C_6$ alkyl)amino, trifluoromethyl, carboxy, $C_1$-$C_6$ alkoxycarbonyl, Ar.sub.I, $Ar_2$—O—, $Ar_2$—S—, $C_3$-$C_7$ cycloalkyl, 2,3-dihydro-1,4-benzodioxinyl, 1H-benzimidazolyl, $C_1$-$C_4$ alkyl-substituted 1H-benzimidazolyl, (1,1'-biphenyl)-4-yl or by 2,3-dihydro-2-oxo-1H-benzimidazolyl; and $R_3$ is hydrogen, nitro, amino, mono- or di-($C_1$-$C_6$ alkyl)amino, halogen, $C_1$-$C_6$ alkyl, hydroxy or $C_1$-$C_6$ alkoxy; wherein $Ar_1$ is phenyl, substituted phenyl, naphthyl, pyridyl, imidazolyl, triazolyl, thienyl, halothienyl, furanyl, $C_1$-$C_6$ alkylfuranyl, halofuranyl or thiazolyl; wherein $Ar_2$ is phenyl, substituted phenyl or pyridyl; and wherein "substituted phenyl" is phenyl that is substituted by up to 3 substituents in each case selected independently of one another from the group consisting of halogen, hydroxy, hydroxymethyl, trifluoromethyl, $C_1$-$C_6$ alkyl, $C_1$-$C_6$ alkoxy, $C_1$-$C_6$ alkoxycarbonyl, carboxy, formyl, hydroxyiminomethyl, cyano, amino, mono- and di-($C_1$-$C_6$ alkyl)amino and nitro.

Individual compounds from that group that may be given special mention are:
(1) 6-[(1H-imidazol-1-yl)-phenylmethyl]-1-methyl-1H-benzotriazole,
(2) 6-[(4-chlorophenyl)(1H-1,2,4-triazol-1-yl)methyl]-1-methyl-1H-benzotriazole.

(s) The compounds of formula II as defined in EP-A-250 198, especially
(1) 2-(4-chlorophenyl)-1,1-di(1,2,4-triazol-1-ylmethyl)ethanol,
(2) 2-(4-fluorophenyl)-1,1-di(1,2,4-triazol-1-ylmethyl)ethanol,
(3) 2-(2-fluoro-4-trifluoromethylphenyl)-1,1-di(1,2,4-triazol-1-ylmethyl)ethanol,
(4) 2-(2,4-dichlorophenyl)-1,1-di(1,2,4-triazol-1-ylmethyl)ethanol,
(5) 2-(4-chlorophenyl)-1,1-di(1,2,4-triazol-1-ylmethyl)-ethanol,
(6) 2-(4-fluorophenyl)-1,1-di(1,2,4-triazol-1-yl-methyl)ethanol.

(t) The compounds of formula I as defined in EP-A-281 283, especially
(1) (1R*2R*)-6-fluoro-2-(4-fluorophenyl)-1,2,3,4-tetrahydro-1-(1H-1,2,4-triazol-1-yl-methyl)naphthalene,
(2) (1R*,2R*)-6-fluoro-2-(4-fluorophenyl)-1,2,3,4-tetrahydro-1-(1H-imidazolylmethyl)-naphthalene,
(3) (1R*,2R*)- and (1R*,2S*)-2-(4-fluorophenyl)-l,2,3,4-tetrahydro-1-(1H-1,2,4-tetrahydro-1-(1H-1,2,4-triazol-1-ylmethyl)naphthalene-6-carbonitrile,
(4) (1R*,2R*)- and (1R*,2S*)-2-(4-fluorophenyl)-l,2,3,4-tetrahydro-1-(1H-imidazolylmethyl)naphthalene-6-carbonitrile,
(5) (1R*,2R*)- and (1R*,2S*)-1,2,3,4-tetrahydro-1-(1H-1,2,4-triazol-1-ylmethyl)-naphthalene-2,6-dicarbonitrile,
(6) (1R*,2R*)- and (1R*,2S*)-1,2,3,4-tetrahydro-1-(1H-imidazol-1-ylmethyl)naphthalene-2,6-dicarbonitrile,
(7) (1R*,2S*)-2-(4-fluorophenyl)-1,2,3,4-tetrahydro-1-(5-methyl-1H-imidazolyl-methyl)naphthalene-6-carbonitrile.

(u) The compounds of formula I as defined in EP-A-296 749, especially
(1) 2,2'-[5-(1H-1,2,4-triazol-1-ylmethyl)-1,3-phenylene]di(2-methylpropiononitrile),
(2) 2,2'-[5-(imidazol-1-ylmethyl)-1,3-phenylene]di(2methylpropiononitrile),
(3) 2-[3-(1-hydroxy-1-methylethyl)-5-(5H-1,2,4-triazol-1-ylmethyl)phenyl]-2-methylpropiononitrile,
(4) 2,2'-[5-dideuterio(1H-1,2,4-triazol-1-yl)methyl-1,3-phenylene]di(2-trideuteriomethyl-3,3,3-trideuteriopropiononitrile),
(5) 2,2'-[5-dideuterio(1H-1,2,4-triazol-1-yl)methyl-3-phenylene]di(2methylpropiononitrile).

(v) The compounds of formula I as defined in EP-A-299 683, especially
(1) (Z)-α-(1,2,4-triazol-1-ylmethyl)stilbene-4,4'-dicarbonitrile,
(2) (Z)-4'-chloro-α-(1,2,4-triazol-1-ylmethyl)stilbene-4-carbonitrile,
(3) (Z)-α-(1,2,4-triazol-1-ylmethyl)-4'-(trifluoromethyl)stilbene-4-carbonitrile,
(4) (E)-.beta.-fluoro-α-(1,2,4-triazol-1-ylmethyl)stilbene-4,4'-dicarbonitrile,
(5) (Z)4'-fluoro-α-(imidazol-1-ylmethyl)stilbene-4-carbonitrile,
(6) (Z)-2',4'-dichloro-α-(imidazol-1-ylmethyl)stilbene-4-carbonitrile,
(7) (Z)-4'-chloro-α-(imidazol-1-ylmethyl)stilbene-4-carbonitrile,
(8) (Z)-α-(imidazol-1-ylmethyl)stilbene-4,4'dicarbonitrile,
(9) (Z)-α-(5-methylimidazol-1-ylmethyl)stilbene-4,4'-dicarbonitrile,
(10) (Z)-2-[2-(4-cyanophenyl)-3-(1,2,4-triazol-1-yl)propenyl]pyridine-5-carbonitrile.

(w) The compounds of formula I as defined in EP-A-299 684, especially
(1) 2-(4-chlorobenzyl)-2-fluoro-1,3-di(1,2,4-triazol-1-yl)propane,
(2) 2-fluoro-2-(2-fluoro-4-chlorobenzyl)-1,3-di(1,2,4-triazol-1-yl)propane,
(3) 2-fluoro-2-(2-fluoro-4-trifluoromethylbenzyl)-1,3-di(1,2,4-triazol-1-yl)propane,
(4) 3-(4-chlorophenyl)-1-(1,2,4-triazol-1-yl)-2-(1,2,4-triazol-1-ylmethyl)butan-2-ol,
(5) 2-(4-chloro-α-fluorobenzyl)-1,3-di(1,2,4-triazol-1-yl)propan-2-ol,
(6) 2-(4-chlorobenzyl)-1,3-bis(1,2,4-triazol-1-yl)propane,
(7) 4-[2-(4-chlorophenyl)-1,3-di(1,2,4-triazol-1-ylmethyl)ethoxymethyl]-benzonitrile,
(8) 1-(4-fluorobenzyl)-2-(2fluoro-4-trifluoromethylphenyl)-1,3-di(1,2,4-triazol-1-yl)-propan-2-ol,
(9) 2-(4-chlorophenyl)-1-(4-fluorophenoxy)-1,3-di(1,2,4-triazol-1-yl)propan-2-ol,
(10) 1-(4-cyanobenzyl)-2-(2,4-difluorophenyl)-1,3di(1,2,4-triazol-1-yl)propan-2-ol,
(11) 2-(4-chlorophenyl)-1-phenyl-1,3-di(1,2,4-triazol-1-yl)propan-2-ol.

(x) The compounds as defined in claim 1 of EP-A-316 097, especially
(1) 1,1-dimethyl-8-(1H-1,2,4-triazol-1-ylmethyl)-2(1H)-naphtho[2,1-b]furanone,
(2) 1,2-dihydro1,1-dimethyl-2-oxo-8-(1H-1,2,4-triazol-1-ylmethyl)naphtho[2,1-b]-furan-7-carbonitrile,
(3) 1,2-dihydro-1,1-dimethyl-2-oxo-8-(1H-1,2,4-triazol-1-ylmethyl)naphtho[2,1-b]-furan-7-carboxamide,
(4) 1,2-dihydro-1,1-dimethyl-2-oxo-8-[di(1H-1,2,4-triazol-1-yl)methyl]naphtho[2,1-b]-furan-7-carbonitrile.

(y) The compounds of formula I as defined in EP-A-354 689, especially
(1) 4-[2-(4-cyanophenyl)-3-(1,2,4-triazol-1-yl)propyl]benzonitrile,
(2) 4-[1-(4-chlorobenzyl)-2-(1,2,4-triazol-1-yl)ethyl]benzonitrile,
(3) 4-[2-(1,2,4-triazol-1-yl)-1-(4-trifluoromethyl]benzyl)ethyl]benzonitrile,
(4) 4-[2-(1,2,4-triazol-1-yl)-1-(4-[trifluoromethoxy]benzyl)ethyl]benzonitrile.

(z) The compounds of formula (1) as defined in EP-A-354 683, especially
(1) 6-[2-(4-cyanophenyl)3-(1,2,4-triazol-1-yl)-propyl]nicotinonitrile,
(2) 4-[1-(1,2,4-triazol-1-yl-methyl)2-(5[trifluoromethyl]pyrid-2-yl)ethyl]benzonitrile.

Examples of steroidal aromatase inhibitors that may be mentioned are:

(aa) The compounds of formula I as defined in EP-A-181 287. These are especially the compounds of formula I

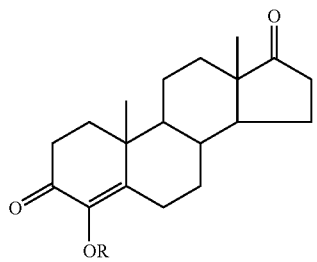

(I)

wherein R is hydrogen, acetyl, heptanoyl or benzoyl. An individual compound from that group that may be given special mention is:
(1) 4-hydroxy-4-androstene-3,17-dione.

(ab) The compounds as defined in the claims of U.S. Pat. No. 4,322,416, especially 10-(2-propynyl)-oestr-4-ene-3,17-dione.

(ac) The compounds as defined in the claims of DE-A-3 622 841, especially 6-methyleneandrosta-1,4-diene-3,17-dione.

(ad) The compounds as defined in the claims of GB-A-2 17 1100, especially 4-amino-androsta-1,4,6-triene-3,17-dione.

Also: (ae) androsta-1,46-triene-3,17-dione.

The content of the patent applications mentioned under (a) to (z) and (aa) to (ad), especially the subgroups of compounds disclosed therein and the individual compounds disclosed therein as examples, have been incorporated by reference into the disclosure of the present application.

The general terms used hereinbefore and hereinafter to define the compounds have the following meanings:

Organic radicals designated by the term "lower" contain up to and including 7, preferably up to and including 4, carbon atoms.

Acyl is especially lower alkanoyl.

Aryl is, for example, phenyl or 1- or 2-naphthyl, each of which is unsubstituted or substituted by lower alkyl, hydroxy, lower alkoxy, lower alkanoyloxy, amino, lower alkylamino, di-lower alkylamino, lower alkanoylamino or by halogen.

Pharmaceutically acceptable salts of the above-mentioned compounds are, for example, pharmaceutically acceptable acid addition salts or pharmaceutically acceptable metal or ammonium salts.

Pharmaceutically acceptable acid addition salts are especially those with suitable inorganic or organic acids, for example strong mineral acids, such as hydrochloric acid, sulfuric acid or phosphoric acid, or organic acids, especially aliphatic or aromatic carboxylic or sulfonic acids, for example formic, acetic, propionic, succinic, glycolic, lactic, hydroxysuccinic, tartaric, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, p-toluenesulfonic, naphthalenesulfonic, sulfanilic or cyclohexylsulfamic acid; or with other acidic organic substances, for example ascorbic acid. Pharmaceutically acceptable salts may also be formed, for example, with amino acids, such as arginine or lysine.

Compounds containing acid groups, for example a free carboxy or sulfo group, can also form pharmaceutically acceptable metal or ammonium salts, such as alkali metal or alkaline earth metal salts, for example sodium, potassium, magnesium or calcium salts, also ammonium salts derived from ammonia or suitable organic amines. Them come into consideration especially aliphatic, cycloaliphatic, cycloaliphatic-aliphatic or araliphatic primary, secondary or tertiary mono-, di- or poly-amines, such as lower alkylamines, for example di- or tri-ethylamine, hydroxy-lower alkylamines, for example 2-hydroxyethylamine, bis(2-hydroxyethyl)amine or tris(2-hydroxyethyl)amine, basic aliphatic esters or carboxylic acids, for example 4-aminobenzoic acid 2-diethylaminoethyl ester, lower alkyleneamines, for example 1-ethylpiperidine, cycloalkylamines, for example dicyclohexylamine, benzylamines, for example N,N'-dibenzylethylenediamine; also heterocyclic bases, for example of the pyridine type, for example pyridine, collidine or quinoline. If several acidic or basic groups are present, mono- or poly-salts can be formed. Compounds according to the invention having an acidic and a basic group may also be in the form of internal salts, i.e. in the form of zwitterions and another part of the molecule in the form of a normal salt.

In the case of the above-mentioned individual compounds the pharmaceutically acceptable salts are included in each case insofar as the individual compound is capable of salt formation.

The compounds listed, including the individual compounds mentioned, both in free form and in salt form, may also be in the form of hydrates, or their crystals may include, for example, the solvent used for crystallisation. The present invention relates also to all those forms.

Many of the above-mentioned compounds, including the individual compounds mentioned, contain at least one asymmetric carbon atom. They can therefore occur in the form of R- or S-enantiomers and as enantiomeric mixtures thereof, for example in the form of a racemate. The present invention relates to the use of all those forms and to the use of all further isomers, and of mixtures of at least 2 isomers, for example mixtures of diastereoisomers or enantiomers which can occur when there are one or more further asymmetric centres in the molecule. Also included are, for example, all geometric isomers, for example cis- and trans-isomers, that can occur when the compounds contain one or more double bonds.

Pharmaceutical Formulations

The pharmaceutical compositions that can be prepared according to the invention are compositions for enteral, such as peroral or rectal administration, also for transdermal or sublingual administration, and for parenteral, for example intravenous, subcutaneous and intramuscular, administration. Suitable unit dose forms, especially for peroral and/or sublingual administration, for example dragees, tablets or capsules, comprise preferably from approximately 0.01 mg to approximately 20 mg, especially from approximately 0.1 mg to approximately 10 mg, of one of the above-mentioned compounds or of a pharmaceutically acceptable salt thereof, together with pharmaceutically acceptable carriers. The preferred form of administration is oral. The proportion of active ingredient in such pharmaceutical compositions is generally from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable oily excipients, such as fatty oils, paraffin oil or liquid polyethylene glycols, to which stabilisers and/or anti-bacterial agents may also be added. There may also be used capsules that are easily bitten through, in order to achieve by means of the sublingual ingestion of the active ingredient that takes place as rapid an action as possible.

Suitable rectally or transvaginally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

Dyes or pigments may be added to the pharmaceutical compositions, especially to the tablets or dragee coatings, for example for identification purposes or to indicate different doses of active ingredient.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragee cores.

The term "improving" as used herein in connection with an effect on implantation or pregnancy includes any measurable improvement or increase in frequency of occurrence of implantation or pregnancy in an individual for example when compared with the level or frequency of occurrence of implantation or pregnancy in one or more non-treated patients or when compared to the level or frequency of occurrence of implantation or pregnancy in the same patient observed at an earlier time point (e.g. comparison with a "base line" level). Preferably the improvement or increase will be a statistically significant one, preferably with a probability value of <0.05. Methods of determining the statistical significance of results are well known and documented in the art and any appropriate method may be used.

EXAMPLES

The invention that is claimed is described in detail in the following Examples, which are intended merely to illustrate the invention, and in no way to represent a limitation thereof.

Example 1

This was a prospective controlled study that included a study group, the patients of which received letrozole (2.5 mg/day from (day 3 to 7 of the menstrual cycle) in addition to FSH and a control group that received FSH only. The study group included 12 unexplained infertility patients. The control group-consisted of 55 unexplained infertility patients. All patients received recombinant or highly purified FSH (50-150 IU/day starting on day 3 to 7 until day of hCG (10,000 IU) that was given when 2 leading follicles were >2 cm). The FSH regimen was based on the patient's clinical profile. Patients were not randomized. All patients had intrauterine insemination. There was no statistically significant difference between the study and control groups as regards age, weight, infertility duration, number of prior insemination cycles, semen parameters or type of FSH.

The FSH needed was statistically significantly lower when letrozole was used in both study group compared with the control group. However, there was no significant difference, in number of follicles >1.8 cm., endometrial thickness, LH level or day of hCG administration. Estradiol level in letrozole/FSH cycles was in the normal physiological range, which was unexpected as higher levels are normally associated with increased follicle production. Pregnancy rate in the study group was 25% versus 18% in the control group. This is indicative of a positive trend in this rate. The study contained too few patients and cycles for the results to be considered to be statistically significant.

TABLE 1

| Treatment | Letrozole + FSH | FSH only | P value |
|---|---|---|---|
| Pregnancy rate | 25% | 18% | NS |
| Total FSH dose/cycle (IU) | 585 | 1320 | <0.05 |
| Day of hCG administration | 12 | 12 | NS |
| Endometrial thickness (on hCG day) | 11.5 | 12.1 | NS |
| Follicle (>1.8 cm) on hCG day | 3.4 | 3.2 | NS |
| Estradiol on hCG day (pmol/L) | 2130 | 3140 | <0.05 |
| Estradiol/mature follicle (pmol/L) | 626 | 969 | <0.05 |
| LH on hCG day (IU/L) | 16.3 | 18.3 | NS |

NS = not significant

Example 2

Fifteen patients who either failed to ovulate (6 cycles) or ovulated with an endometrial thickness <5 mm (24 cycles) in response to CC and who did not conceive were given letrozole orally, at least two months after the last CC cycle, in a dose of 2.5 to 5 mg/day, from day 3 to 7 or 5 to 9 of the menstrual cycle. HCG 10,000 IU was given to trigger ovulation. CC was given in a dose of 50-100 mg on days 3-7 or 5-9.

Fifteen patients completed 17 letrozole cycles. Ovulation occurred in 13 cycles (77%) and pregnancy in 5 out of 15 patients (33%). The following table shows summary of CC and letrozole cycles.

TABLE 2

| Treatment | Mean | | | Range | | Median | |
|---|---|---|---|---|---|---|---|
| | Letrozole | CC | P | Letrozole | CC | Letrozole | CC |
| Day of hCG administration | 14.5 | 12.6 | S | 11-18 | 11-16 | 15 | 12 |
| Number of Days from last letrozole tablet to hCG day | 6.7 | 4.4 | S | 2-9 | 2-7 | 7 | 4 |
| Endometrial Thickness (Cm.) | 0.8 | 0.5 | S | 0.6-1.1 | 0.4-0.8 | 0.8 | 0.4 |
| Follicles > 1.5 Cm on day of hCG administration | 2.4 | 1.9 | NS | 1-3 | 1-5 | 2 | 2 |
| Estradiol (pmol/L) on day of hCG administration | 1016 | 2145 | S | 107-2347 | 362-5210 | 901 | 1668 |
| Estradiol per mature follicle (pmol/L) | 392 | 1278 | S | 107-837 | 177-2404 | 289 | 1486 |
| LH on day of hCG administration (IU/L) | 16 | 16 | NS | 3.1-66 | 3-66 | 8.2 | 8 |

P value (<0.005 = significant)

S = Significant

NS = Not Significant

These results illustrate the improvement letrozole offers over CC in relation to endometrial thickness and reduced estradiol levels. The results suggest improved pregnancy levels.

Example 3

This example demonstrates the effect of letrozole alone in a single dose form of administration. The estradiol levels in 9 treatment cycles in 7 infertile patients (3 with PCOS and 4 with unexplained infertility) undergoing ovarian stimulation and cycle monitoring for IUI who received a single 20 mg dose of letrozole on day 3 of the cycle. Follicle development was monitored by transvaginal ultrasound and by serum levels of estradiol and LH. Pregnancy was achieved in one patient. The mean estradiol level on the day of hCG was 831 pmol/L and the mean estradiol level per mature follicle was 390 pmol/L, almost exactly the same as seen with a 5-day daily dose of letrozole illustrated in the previous example.

TABLE 3

| | Letrozole single-dose cycles |
|---|---|
| Day of hCG administration | 12.9 (2.9) |
| Endometrial thickness on hCG day (cm) | 0.9 (0.11) |
| Follicles > 1.5 cm | 2.29 (1.3) |
| Estradiol on hCG day (pmol/L) | 831 (359) |
| Estradiol/mature follicle (pmol/L) | 390 (74) |
| LH (IU/L) | 19.1 (12.7) |

Example 4

Superovulation for IUI with Letrozole and FSH

Patient Group: 19 Women with unexplained fertility, 6 with PCOS, 2 with endometriosis and one with male factor Protocol: Study group received Letrozole (2.5 to 5 mg/day, days 3 to 7) and FSH (dose adjusted to need, starting on day 3, 5 or 7); hCG (10,000 bolus). Control group received FSH alone.

Fertilisation Method: IUI

Endpoints: Pregnancy rate, endometrial thickness, follicles >1.5 cm on hCG day, estradiol on hCG day, total FSH dose Results: Pregnancy rate with Letrozole and FSH was 38% (not reported for FSH alone), endometrial thickness was the same in both groups, number of follicles >1.5 cm was the same, estradiol was 45% lower in Letrozole group, total FSH dose was decreased by 77% in Letrozole group

Example 5

Letrozole for Ovulation Induction: Summary

Patient Group: PCOS and unexplained infertility undergoing IUI.

Protocol: Study group 1 PCOS patients received Letrozole (2.5 to 5 mg/day, days 3 to 7); hCG bolus 10,000 I.U. Control group 1 PCOS patients received CC (50-100 mg/day, days 3 to 7 or days 5 to 9); hCG bolus 10,000 I.U. Study group 2 unexplained infertility patients received Letrozole (2.5 mg/day, days 3 to 7) plus FSH (50-150 I.U., starting on days 3 to 7 until hCG); hCG bolus 10,000 I.U. Control group 2 unexplained infertility patients received CC (50-100 mg/day, days 3 to 7) plus FSH (50-150 I.U., starting on day 3 to 7 until hCG); hCG bolus 10,000 I.U.

Fertilisation Method: Timed intercourse or IUI

Endpoints: Pregnancy rate, ovulation rate, endometrial thickness, follicles >1.5 cm on hCG day, oestradiol on hCG day.

Results: Pregnancy rate was higher with Letrozole VS CC in both kinds of regimen, ovulation rate was higher with Letrozole VS CC in PCOS patients (not reported for unexplained fertility), endometrial thickness was better with Letrozole.

While the invention has been described with particular reference to certain embodiments thereof, it will be understood that changes and modifications may be made by those of ordinary skill in the art within the scope and spirit of the following claims.

In the claims, the word "comprising" means "including the following elements (in the body), but not excluding others"; the phrase "consisting of" means "excluding more than traces of other than the recited ingredients"; and the phrase "consisting essentially of" means "excluding unspecified ingredients which materially affect the basic characteristics of the composition".

REFERENCES

[1] Hadi, F. H., Chantler, E., Anderson, E. et al. (1994) Ovulation induction and endometrial steroid receptors. Hum. Reprod., 9, 2405-2410.

[2] Paulson, R. J., Sauer, M. V. and Lobo, R. A. (1990) Factors affecting embryo implantation after human in vitro fertilization: a hypothesis. Am. J. Obstet. Gynecol., 163, 2020-2023; Simón, C., Cano, F., Valbueña, D. et al. (1995) Clinical evidence for a detrimental effect on uterine receptivity of high serum oestradiol concentrations in high and normal responder patients. Hum. Reprod., 10, 2432-2437; Ng. E. H. Y., Yeung, W. S. B., Lau, E. Y. and Ho, P. C. (2000) High serum oestradiol concentration in fresh IVF cycles do not impair implantation and pregnancy rates in subsequent frozen-thawed embryo transfer cycles. Hum. Reprod., 15, 250-255.

[3] Ng, Yeung, Lau and Ho, *High serum oestradiol concentration in fresh IVF cycles do not impair implantation and pregnancy rates in subsequent frozen-thawed embryo transfer cycles*. p. 15, 250-255.

[4] Ghazala Sikandar Basir G S, Wai-sum O, Ng E H and Ho P C. Morphometric analysis of peri-implantation endometrium in patients having excessively high oestradiol concentrations after ovarian stimulation. Hum Reprod, 2001; 16(3): 435-40; Forman, R., Fries, N., Testart, J. et al. (1988) Evidence for an adverse effect of elevated serum estradiol concentration on embryo implantation. Fertil. Steril., 49, 118-112.

[5] Garcia, J. E., Acosta, A. A., Hsiu, J. G. and Jones, H. W. J. (1984) Advanced endometrial maturation after ovulation induction with human menopausal gonadotropin/human chorionic gonadotropin for in vitro fertilization. Fertil. Steril., 41, 31-35; Graf, M. J., Reyniak, J. V., Battle, M. P. and Laufer, N. (1988) Histologic evaluation of the luteal phase in women following follicle aspiration for oocyte retrieval. Fertil. Steril., 49, 616-619.

[6] Sterzik, K., Dallenbach, C., Schneider, V. et al. (1988) In vitro fertilization: the degree of endometrial insufficiency varies with the type of ovarian stimulation. Fertil. Steril., 50, 457-462; Seif, M. W., Pearson, J. M., Ibrahim, Z. H. et al. (1992) Endometrium in in-vitro fertilization cycles: morphological and functional differentiation in the implantation phase. Hum. Reprod., 7, 6-11.

[7] Kolb, B. A., Najmabadi, S. and Paulson, R. J. (1997) Ultrastructural characteristics of the luteal phase endometrium in patients undergoing controlled ovarian stimulation. Fertil. Steril., 67, 625-630.

[8] Macrow, P. J., Li, T. C., Seif, M. W. et al. (1994) Endometrial structure after superovulation: a prospective controlled study. Fertil. Steril., 61, 696-699.

[9] Noci, I., Borri, P., Coccia, M. E. et al. (1997) Hormonal patterns, steroid receptors and morphological pictures of endometrium in hyperstimulated IVF cycles. Eur. J. Obstet. Gynecol. Reprod. Biol., 75, 215-220.

[10] Forman, Fries and Testart, *Evidence for an adverse effect of elevated serum estradiol concentration on embryo implantation*. p. 49, 118-112.

[11] Geeta Nargund, John Waterstone, J. Martin Bland, Zoe Philips, John Parsons, and Stuart Campbell Cumulative conception and live birth rates in natural (unstimulated) IVF cycles Hum. Reprod. 2001 16: 259-262.

[12] Valbuena D, Martin J, de Pablo J L, Remohi J, Pellicer A, Simon C. Increasing levels of estradiol are deleterious to embryonic implantation because they directly affect the embryo. Fertil Steril 2001; 76:962-8.

[13] Simón, C., Garcia, V. J., Valbueña, D. et al. (1998) Increasing uterine receptivity by decreasing estradiol levels during the preimplantation period in high responders with the use of a follicle-stimulating hormone step-down regimen. Fertil. Steril., 70, 234-239.

[14] Tortoriello D V, McGovern P G, Colon J M, Skurnick J H, Lipetz K, Santoro N. "Coasting" does not adversely affect cycle outcome in a subset of highly responsive in vitro fertilization patients. Fertil Steril. 1998 March; 69(3):454-60.

The invention claimed is:

1. A method for improving the implantation and/or pregnancy rate for a female patient undergoing assisted reproduction treatment, which comprises administering one or more daily doses of an aromatase inhibitor (AI) selected from the group consisting of anastrozole, letrozole and vorozole during an assisted reproduction cycle, wherein the doses of AI are selected from amounts effective to reduce serum estradiol levels, wherein the AI is administered starting on any one of days 1 to 5 of a menstrual cycle, and wherein the assisted reproduction treatment is selected from the group consisting of in vitro fertilization (IVF), Gamete Intrafallopian Transfer Procedure (GIFT), Zygote Intrafallopian Transfer Procedure (ZIFT), Intracytoplasmic Sperm Injection (ICSI), Intrauterine Insemination (IUI), and Therapeutic Donor Insemination (TDI).

2. The method of claim 1, wherein the aromatase inhibitor is administered in a regimen using FSH or a mixture of FSH and LH.

3. The method of claim 1, wherein the aromatase inhibitor is administered with a plurality of daily doses of FSH or a mixture of FSH and LH.

4. The method of claim 1, wherein the aromatase inhibitor is administered in 1 to 10 daily doses.

5. The method of claim 1, wherein the aromatase inhibitor is administered on each of days 3 to 7 of the menstrual cycle.

6. The method of claim 1, wherein the aromatase inhibitor is administered on each of days 5 to 9 of the menstrual cycle.

7. The method of claim 1, wherein the aromatase inhibitor is administered in a daily dose of from about 1 mg to about 10 mg.

8. The method of claim 1, wherein the aromatase inhibitor is letrozole and is administered in a daily dose of from about 2.5 mg to about 10 mg.

9. The method of claim 1, wherein the aromatase inhibitor is anastrozole and is administered in a daily dose of from about 1 mg to about 4 mg.

10. The method of claim 1, wherein the aromatase inhibitor is vorozole and is administered in a daily dose of from about 2 mg to about 8 mg.

11. The method of claim 1, wherein the aromatase inhibitor is administered as a single dose selected from amounts in the range of from about 5 mg to about 500 mg.

12. The method of claim 1, wherein the aromatase inhibitor is administered as a single dose selected from amounts in the range of from about 10 mg, 20 mg, 25 mg or 30 mg to about 500 mg.

13. The method of claim 1, wherein the aromatase inhibitor is administered at an amount that lowers estradiol levels to post-menopausal levels in a female.

14. The method of claim 1, wherein the aromatase inhibitor is administered at an amount that lowers estradiol levels to about 100 pmol/L or less.

15. The method of claim 1, wherein the aromatase inhibitor is administered at an amount that lowers estradiol levels to about normal physiologic pre-implantation levels in a female.

16. The method of claim 1, wherein the aromatase inhibitor is administered at an amount that lowers estradiol levels to less than or equal to about 10,000 pmol/L.

17. The method of claim 1, wherein the aromatase inhibitor is administered at an amount that lowers estradiol levels to within the range of from about 300 pmol/L to about 5000 pmol/L.

18. The method of claim 1, wherein the aromatase inhibitor is administered orally.

19. The method of claim 2, wherein FSH or a mixture of FSH and LH is used in a daily dose ranging from about 25 I.U. FSH to about 600 I.U. FSH.

20. The method of claim 2, wherein FSH or a mixture of FSH and LH is used in a daily dose ranging from about 50 I.U. FSH to about 225 I.U. FSH.

21. The method of claim 2, wherein FSH or a mixture of FSH and LH is used in a daily dose ranging from about 50 I.U. FSH to about 150 I.U. FSH.

22. The method of claim 2, wherein the aromatase inhibitor and FSH or mixture of FSH and LH are administered simultaneously, separately or sequentially.

23. The method of claim 1, wherein the patient is selected from the group consisting of patients who are of reproductive age; who are poor responders to FSH; who do not ovulate with clomiphene citrate; who would show an endometrial thickness of less than 5 mm after a cycle of clomiphene citrate; who suffer from unexplained infertility; who suffer from polycystic ovary syndrome (PCOS); who suffer from endometriosis; who suffer from cervical mucus abnormalities; who suffer from increased baseline FSH concentration; who suffer from elevated FSH concentration; who suffer from male factor infertility; and older patients.

24. The method of claim 1, wherein a GnRH agonist is administered to the patient.

25. The method of claim 1, wherein a GnRH antagonist is administered to the patient.

* * * * *